US012620464B2

(12) United States Patent
Dominick et al.

(10) Patent No.: US 12,620,464 B2
(45) Date of Patent: May 5, 2026

(54) METHOD AND SYSTEM FOR PROVIDING A MEDICAL REPORT

(71) Applicant: Siemens Healthineers AG, Forchheim (DE)

(72) Inventors: Lutz Dominick, Eggolsheim (DE); Vladyslav Ukis, Nuremberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 175 days.

(21) Appl. No.: 18/159,243

(22) Filed: Jan. 25, 2023

(65) Prior Publication Data

US 2023/0238096 A1 Jul. 27, 2023

(30) Foreign Application Priority Data

Jan. 27, 2022 (DE) ..................... 10 2022 200 925.8

(51) Int. Cl.
| | |
|---|---|
| G16H 15/00 | (2018.01) |
| G16H 10/60 | (2018.01) |
| G16H 30/40 | (2018.01) |

(52) U.S. Cl.
CPC ............. G16H 15/00 (2018.01); G16H 10/60 (2018.01); G16H 30/40 (2018.01)

(58) Field of Classification Search
CPC ........ G16H 15/00; G16H 10/60; G16H 30/40; G16H 50/70
See application file for complete search history.

(56) References Cited

U.S. PATENT DOCUMENTS

| | | | |
|---|---|---|---|
| 2005/0144042 A1* | 6/2005 | Joffe | G16H 10/60 705/2 |
| 2013/0223708 A1* | 8/2013 | Fukatsu | G06T 7/0012 382/128 |
| 2013/0325497 A1* | 12/2013 | Kanada | G16H 15/00 705/2 |
| 2014/0350961 A1 | 11/2014 | Csurka et al. | |
| 2020/0160970 A1* | 5/2020 | Lyman | G06V 10/25 |
| 2020/0211692 A1* | 7/2020 | Kalafut | G06F 40/30 |
| 2020/0243173 A1* | 7/2020 | Yoshida | G06Q 10/10 |
| 2020/0246543 A1* | 8/2020 | Sadeghzadeh | A61B 5/7435 |
| 2022/0253592 A1* | 8/2022 | Rao | G16H 30/20 |
| 2022/0270729 A1* | 8/2022 | Saliman | H04L 9/0894 |

FOREIGN PATENT DOCUMENTS

| | | | |
|---|---|---|---|
| WO | WO-2021045996 A1 * | 3/2021 | G06F 40/169 |

OTHER PUBLICATIONS

Lee et al., Enhancement of Structured Reporting—an Integration Reporting Module with Radiation Dose Collection Supporting, Oct. 4, 2016, Journal of Medical Systems, vol. 40, Article 250, pp. 1-8. (Year: 2016).*

* cited by examiner

*Primary Examiner* — Christopher L Gilligan
(74) *Attorney, Agent, or Firm* — Harness, Dickey & Pierce, P.L.C.

(57) ABSTRACT

One or more example embodiments of the present invention relates to methods and apparatuses for providing a medical report in a medical network having a front-end computing facility and a back-end computing facility.

18 Claims, 9 Drawing Sheets

METHOD AND SYSTEM FOR PROVIDING A MEDICAL REPORT

CROSS-REFERENCE TO RELATED APPLICATION(S)

The present application claims priority under 35 U.S.C. § 119 to German Patent Application No. 10 2022 200 925.8, filed Jan. 27, 2022, the entire contents of which are incorporated herein by reference.

FIELD

One or more example embodiments of the present invention relates to methods and systems for providing a medical report.

RELATED ART

The aim of medical diagnostics is to prove or rule out a suspected diagnosis. The aim of the diagnostic process is to determine the condition of the patient with regard to a variety of clinical aspects, with imaging methods (for instance, radiological or histopathological imaging) or other clinical methods (for example, laboratory investigations) being used as evidence. In this process the diagnostic tasks of the doctor consist in analyzing patient data and identifying positive as well as negative clinical diagnoses. The doctor's tasks also include qualifying something (for example, as malignant), quantifying something (for example, the spatial extent, or the volume) and comparing current diagnoses with earlier diagnoses.

Furthermore, one task consists in documenting diagnoses to enable the further use of the diagnostic results. For this purpose, a medical report is generated in medical practice. Another term for medical report is, for example, findings report or also doctor's letter. Medical reports are frequently created during analysis of the patient data by the doctor making the diagnosis.

SUMMARY

One problem of instantaneous processes lies firstly in the availability of medical reports that have already been created in a medical (information) network or within a medical organization such as a hospital or a hospital group. Medical reports are frequently locally generated, saved and managed, and only made available to directly involved doctors. In other words, once created, medical reports remain in "silos". A systematic comparison with earlier medical reports is made considerably difficult thereby.

A further problem is given in that medical staff frequently do not receive any feedback about where and how a medical report is used and what changes are made to the report. Furthermore, with the instantaneous practice it is not possible to keep existing medical reports systematically up-to-date and adjust them, for instance, to new knowledge (for instance, due to new patient data or the availability of new analysis tools). The medical reports, once created, remain ostensibly "valid". When accessing such obsolescent reports there is therefore a risk of incorrect conclusions being drawn and incorrect decisions being made.

A further problem is often given by a lack of standardization of medical reports, which makes a comparison between different medical reports difficult.

A further problem lies, moreover, in the enormous volume of data, which a doctor has to take into account when diagnosing a patient. A wide variety of partially orthogonal information has to be screened to make a diagnosis—from image data about laboratory data through to anamnesis data. In practice the doctor has to successively retrieve and screen individual datasets of a patient from different storage facilities within the medical network in order to decide whether an item of individual information contained therein is relevant to the medical report to be created.

Example embodiments of the invention solve said problems and provide methods and systems with which an improved provision or creation of medical reports is possible when diagnosing a patient. In particular, a solution is to be created, which enables simplified integration of patient data in the report generation workflow and improved data management of existing medical reports in accordance with the circumstances of medical information networks.

According to one or more example embodiments, a method for providing a medical report in a medical network having a front-end computing facility and a back-end computing facility, includes receiving context information based on a patient, the receiving receives the context information from the front-end computing facility at the back-end computing facility; providing patient data of the patient on the back-end computing facility; providing at least one data filter using the back-end computing facility based on the context information, the at least one data filter being configured to extract at least one item of individual information from the patient data for generating a medical report; generating the medical report based on the patient data and the context information using the back-end computing facility by applying the at least one data filter to the patient data; and communicating the medical report to the front-end computing facility using the back-end computing facility.

According to one or more example embodiments, the providing the at least one data filter includes providing a plurality of selection data filters in the back-end computing facility, the selection data filters being configured to extract different items of individual information respectively for creating different medical reports, and selecting the at least one data filter from the selection data filters.

According to one or more example embodiments, the at least one data filter comprises a trained function, the trained function being configured to extract at least one item of individual information for generating a medical report based on the context information.

According to one or more example embodiments, the method further includes providing a selection of a plurality of selection templates for creating different medical reports, respectively; and selecting a template from the plurality of selection templates based on the context information, wherein the generating generates the medical report based on the template.

According to one or more example embodiments, providing an earlier version of the medical report for the patient on the back-end computing facility; and ascertaining an item of change information based on a comparison between the patient data and the earlier version of the medical report, the change information indicating how at least one condition of the patient has changed since an instance of the earlier version of the medical report, wherein the generating generates the medical report further based on the change information.

According to one or more example embodiments, the method further includes determining at least one earlier application instance of the earlier version of the medical report in the medical network; and communicating the medical report to the at least one earlier application instance.

According to one or more example embodiments, the method further includes ascertaining at least one missing item of individual information in the patient data based on at least one of the context information or the at least one data filter; and at least one of (i) communicating a note relating to the at least one missing item of individual information to the front-end computing facility, (ii) applying a data evaluation program for ascertaining the at least one missing item of individual information on the back-end computing facility, or (iii) prompting at least one of the front-end computing facility or a different application instance in the medical network to ascertain the at least one missing item of individual information using the back-end computing facility.

According to one or more example embodiments, the patient data comprises at least one medical image dataset, the at least one missing item of individual information refers to a measured value to be extracted from the at least one medical image dataset, and the data evaluation program is an image processing algorithm for extracting the measured value from the at least one medical image dataset.

According to one or more example embodiments, the at least one missing item of individual information refers to an examination of the patient that has not been performed, and the prompting is performed, the prompting including prompting performance of the medical examination that has not been performed.

According to one or more example embodiments, the method further includes receiving a modified medical report from the front-end computing facility on the back-end computing facility, the modified medical report being based on the medical report and the modified medical report includes one or more modifications compared to the medical report; and adjusting the at least one data filter based on a comparison between the modified medical report and the medical report.

According to one or more example embodiments, the method further includes detecting an update event with respect to the medical report on the back-end computing facility; updating the medical report in accordance with the update event; and communicating the updated medical report to the front-end computing facility, wherein the update event comprises at least one of the following events, providing updated patient data, providing an adjusted data filter, receiving an update request in the back-end computing facility from the medical network, or expiration of a specified period since generation of the medical report.

According to one or more example embodiments, the method further includes determining at least one further application instance of the medical report in the medical network different from the front-end computing facility; and communicating the updated medical report to the at least one further application instance.

According to one or more example embodiments, an apparatus for providing a medical report in a medical network having at least one front-end computing facility, wherein the apparatus is connected to the front-end computing facility via the medical network, the apparatus comprises a computing facility, the computing facility configured to cause the apparatus to receive context information based on a patient, the context information being from the front-end computing facility, provide patient data of the patient, provide at least one data filter based on the context information, the at least one data filter being configured to extract at least one item of individual information from the patient data for generating a medical report, generate the medical report based on the patient data and the context information by applying the at least one data filter to the patient data, and communicate the medical report to the front-end computing facility.

According to one or more example embodiments, a non-transitory computer-readable storage medium includes readable and executable program segments, when executed by a computing facility, cause the computing facility to perform a method of according to one or more example embodiments.

Advantages are achieved by methods, systems, computer program products or computer-readable storage media as claimed in the main claim and the coordinating claims. Advantageous developments are disclosed in the dependent claims.

BRIEF DESCRIPTION OF THE DRAWINGS

Further particularities and advantages will become obvious from the following explanations of exemplary embodiments on the basis of schematic drawings. Modifications mentioned in this connection can be respectively combined with each other to form new embodiments. Identical reference characters will be used in different figures for identical features.

In the drawings.

DETAILED DESCRIPTION

Figure 1:
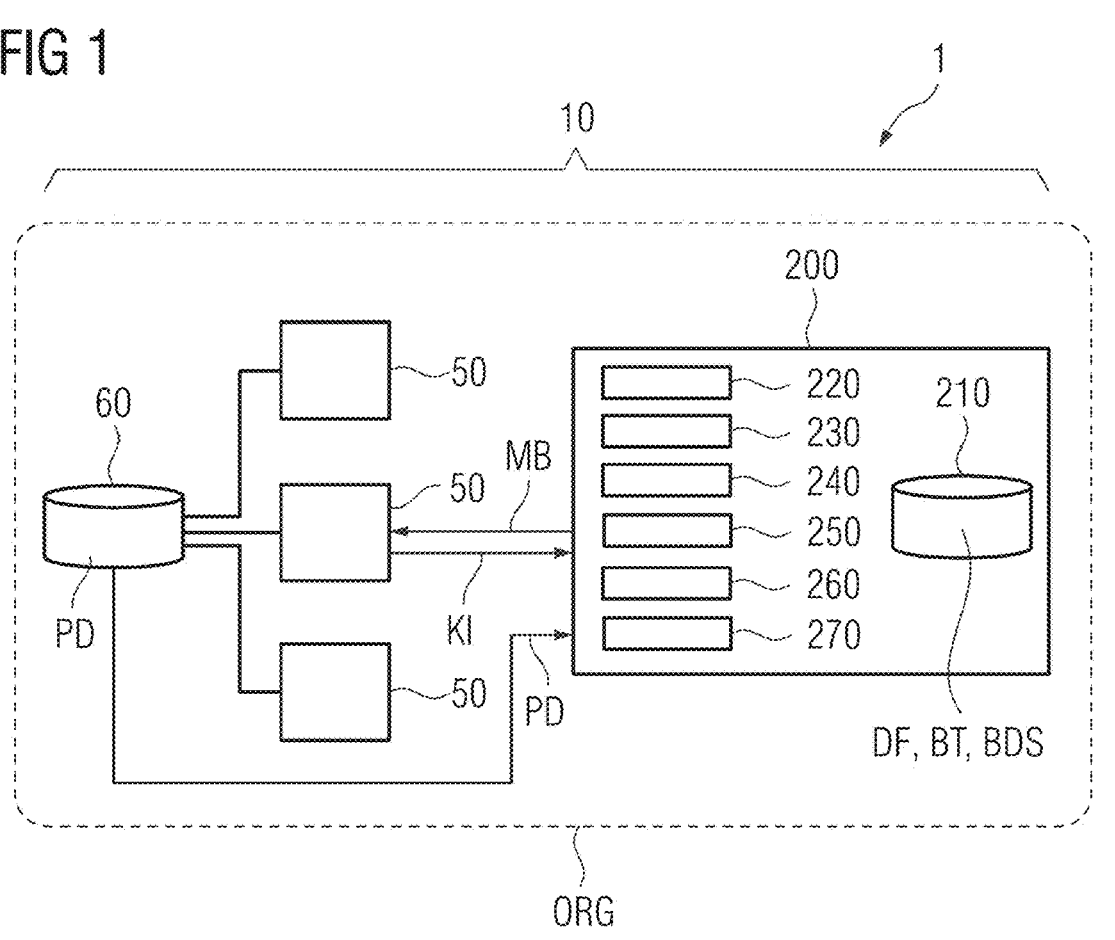
FIG. 1 shows a schematic representation of an embodiment of a system for providing a medical report according to one embodiment.

Advantages or alternative embodiments/aspects mentioned in this connection should likewise also be transferred to the claimed subject matters, and vice versa. In other words, the concrete claims (which are directed, for example, to a system) can also be developed with the features, which are described or claimed in connection with a method. The corresponding functional features of the method can be embodied by corresponding concrete modules.

Furthermore, an inventive solution to the object will also be described in relation to methods and apparatuses for adjusting trained functions. Features and alternative embodiments/aspects of data structures and/or functions in the case of methods and apparatuses in the application of a trained function can be transferred to analogous data structures and/or functions in the case of methods and apparatuses for the purpose of adjusting. Analogous data structures can be identified here in particular by the use or the prefix "training". Furthermore, the trained functions used in methods and apparatuses can have been adjusted and/or provided in particular by methods and apparatuses for adjusting trained functions.

In accordance with one aspect, a method for providing a medical report in a medical network is provided. The medical network has at least one front-end computing facility and one back-end computing facility. The method comprises a plurality of steps. One step is directed toward receiving context information, based on a patient, from the front-end computing facility on the back-end computing facility. One step is directed toward providing patient data of the patient on the back-end computing facility. A further step is directed to providing at least one data filter on the basis of the context information by way of the back-end computing facility, wherein the data filter is designed to extract from patient data at least one item of individual information for generating a medical report. A further step is directed toward generating the medical report on the basis of the patient data and the context information by way of the back-end computing facility by applying the data filter to the patient data. A further step is directed toward transferring the medical report to the front-end computing facility by way of the back-end computing facility.

The medical network or medical information network can be designed for the exchange of medical information, in particular context information, patient data, medical reports and the like, therefore. The medical network can establish a communication or/or data link, in particular between the front-end computing facility and the back-end computing facility. In addition, the medical network can establish a communication and/or data link to further facilities of the medical data processing such as storage facilities for storing patient data or medical reports. The medical network can comprise an Intranet and/or an Internet. In other words, the front-end computing facility can have a communication or/or data link to the back-end computing facility via the Internet. Furthermore, the back-end computing facility can be provided with the context information and/or the patient data via the Internet (by way of the front-end computing facility). Conversely, the medical report can be communicated to the front-end computing facility via the Internet (by way of the back-end computing facility).

In accordance with embodiments, communication or data links can be based on the HL7 standard. Health Level 7 (HL7) is a group of international standards for the exchange of data between organizations in the public health system and its computer systems. In particular, communication and/or data links can be based on the FHIR standard. Fast Healthcare Interoperability Resources (FHIR) is a standard compiled by HL7. It supports data exchange between software systems in the public health system. By using the HL7 or FHIR standards, data can be transferred in a structured manner and no reformatting is necessary.

The front-end computing facility can be designed in particular as a diagnostic workstation or diagnostic station, on which a user (in particular a medical professional such as a doctor) can call up and/or screen and/or analyze patient data and/or on which the user can call up and/or screen and/or modify medical reports. For this purpose, the front-end computing facility can have a user interface. The front-end computing facility can be designed as what is known as a client.

The back-end computing facility can be designed as a server system. The back-end computing facility can have a cluster or a group of computing facilities and data memories. The back-end computing facility cannot have a user interface for the user (the front-end computing facility). The back-end computing facility can have a data link to the front-end computing facility via the medical network. The back-end computing facility can have data link to a plurality of different (but in particular, similar) front-end computing facilities via the medical network. The front-end computing facility (facilities) can belong to a medical organization, such as a practice, a hospital or a hospital group. The back-end computing facility can likewise belong to a medical organization or be designed outside of the medical organization. The back-end computing facility can have a data link to a plurality of different front-end computing facilities, which belong to different medical organizations respectively, via the medical network.

The patient data contains the available medical data on the patient. The medical data can comprise medical image data as well as non-image data. Image data can refer in this connection to medical image data having two or three spatial dimensions. Furthermore, the image data can also have a time dimension. Medical image data is in particular image data, which was recorded with an imaging modality and can represent in particular a body part of the patient. Imaging modalities can comprise, for example, computed tomography devices, magnetic resonance devices, X-ray devices, ultrasound devices and the like. Image data recorded with such or similar modalities is also referred to as radiology image data. Furthermore, medical image data can comprise digitalized histopathology images, which represent a correspondingly prepared tissue section of the patient. The image data can also comprise longitudinal data in the form of time series or temporally spaced-apart follow-up scans, for instance.

Non-image data can comprise data, in particular longitudinal data, which includes one or more medical value(s) of the patient and/or elements from the case history of the patient. This can be laboratory data, vital signs and/or other measured values or preliminary examinations based on the patient. Furthermore, the non-image data can comprise the demographic details based on the patient based on the age, sex, lifestyle habits, risk factors, etc., for instance. In addition, non-image data can have one or more preliminary diagnoses and/or other assessments (for instance, of other, possibly referring doctors). These can be included in the patient data, for example in the form of one or more structured or unstructured medical report(s).

The patient data can be retrieved from one or more storage facility(ies), which storage facilities can be incorporated in the medical network. For example, the user can select a diagnosis task or a patient from a work list on the front-end computing facility. The user can be, for example, a doctor, such as a radiologist, who wishes to make a medical diagnosis for the patient (the patient will hereinafter also be called "patient to be diagnosed"). On the basis of the selection of the diagnosis task or the patient, the connected storage facilities can be interrogated about the patient data of the patient (for example, by the back-end computing facility or the front-end computing facility). For example, an electronic identifier, such as a patient-ID or an access number, can be used for this purpose. The patient data can accordingly be received from one or more of the available storage facility(ies) in which at least parts of the patient data respectively are saved. The storage facilities can be, for example, part of medical information systems, such as hospital information systems and/or PACS systems and/or laboratory information systems, etc.

According to some embodiments of the invention, the patient data can have very comprehensive and varied information about the health of the patient (but according to other embodiments/aspects can also be limited to one data category—for instance, image data and in particular radiology image data in this case). In the context of a diagnosis task it can be a task of the user to make a medical finding or a medical diagnosis or draw a conclusion based on the patient data and to create a medical report.

A medical report can be the result of a diagnostic process, which is aimed at determining the condition of a patient with regard to a large number of clinical aspects on the basis of the patient data relevant to this. A medical report can have in particular a structured document. Imaging methods or methods of diagnostic radiology or of digital histopathology imaging are frequently used in modern medicine for this purpose. In addition, non-image data, such as laboratory data, demographic data, anamnesis data, preliminary findings, etc. are taken into account. The aim is to confirm or rule out a suspected diagnosis. Data, in particular, for example, X-ray images, magnetic resonance scans or ultrasound scans, histopathology images produced by the imaging method can form part of the medical report and is conducive in particular for documentation and transparency of the diagnostic process. Similarly, non-image data can be included in the medical report. The data for a medical report selected in this way from the entirety of the patient data is also referred as individual information in the context of one or more example embodiments of the present invention.

Furthermore, data can also be derived from said patient data by means of data processing. This can be, for example, measured values (for instance, volumes, distances, contrast values, surface ratios, etc.) extracted, in particular automatically, from image data or measured values (trends, absolute values, etc.) extracted, in particular automatically, from non-image data. Data of this kind is also referred to as individual information. In addition, it falls to a doctor or another suitable expert to interpret or evaluate the patient data or individual information with regard to clinical pictures. The results of the evaluation of the patient data can also be incorporated in the medical report as items of individual information (or modified items of individual information). In other words, items of individual information can be information, which is extracted or produced, either automatically or by a user, from the patient data in order to create a medical report. Items of individual information can conventionally result in a medical conclusion. A medical report can have in particular a structured document, which in turn has one or more item(s) of individual information.

Context information (other words are report context or diagnosis context) summarizes the boundary conditions, which are relevant to a particular diagnostic activity of the user. Context information can refer to the report to be created and define, for example, which items of individual information the report should contain and possibly their order. Context information can comprise details about the diagnostic activity, the diagnosis task, the health status of the patient, the urgency of the task, etc. Furthermore, the context information can comprise a list or another suitable data structure in which datasets within the patient data are listed, which are to be used, for example owing to a diagnosis task. The context information can be selected from a large number of items of context information for a particular diagnostic activity or diagnosis task. This is to say that for each diagnostic activity, a particular item of context information can be selected, which requests or retrieves the patient data or items of individual information required for the execution of the diagnostic activity. The back-end computing facility can be provided with the diagnostic activity or diagnosis task by the front-end computing facility, for example.

From the available patient data the data filter is designed to identify and provide items of individual information, which are necessary for creating a medical report corresponding to the context information. The data filter can be, for example, a, in particular adaptive, data evaluation algorithm. The data filter can identify, for example, individual datasets in the patient data and provide them as items of individual information and/or process individual datasets further and provide the result of processing as individual information. In other words, the data filter can map the context information on a set of commands, which identifies and provides suitable items of individual information in the patient data.

Providing the medical report by way of the back-end computing facility means the medical report is provided by a central instance within the medical network. In other words, a method is implemented, which provides the medical report "ss a service". Consequently medical reports can be standardized and updates, for instance in the patient data or data filters, can be easily taken into account. Furthermore, dynamic version management of medical reports in the network is enabled thereby. In addition, the user is assisted in the screening and selection of suitable items of individual information. An infrastructure is provided therefore, which was specifically adapted to the problem with the split into front-end computing facility and back-end computing facility. The components are addressed, moreover, in a manner which is determined by technical circumstances of medical systems, for instance in the sense that a plurality of front-end computing facilities, on which the diagnosis takes place, have to be coordinated in a medical network.

According to one aspect, providing the patient data comprises the following steps:

extracting a patient identifier from the context information;

interrogating at least one storage facility in the medical network about patient data pertaining to the patient on the basis of the patient identifier by way of the back-end computing facility;

receiving the patient data on the back-end computing facility.

By way of said aspect the patient data can be centrally interrogated, and this ensures firstly that all relevant data is taken into account and secondly, unburdens the user.

The storage facility can have a plurality of individual and, in particular, mutually independent memory units in which different patient data of the patient can be saved respectively, such as medical image data in an image data memory unit (for instance, a PACS system), laboratory data in a laboratory data memory unit (for instance, an LIS system) or further health data of the patient in a health data memory unit (for instance, an EMR system).

According to one aspect, the patient data comprises medical image datasets and laboratory datasets of the patient and the data filter is designed in such a way as to provide a first item and a second item of individual information, with the first item of individual information being extracted from the medical image datasets and the second item of individual information being extracted from the laboratory datasets. The medical report can thus be automatically created on the basis of complementary information.

According to one aspect, the step of providing the at least one data filter comprises:

provide a plurality of different selection data filters in the back-end computing facility, which selection data filters are designed to extract different items of individual information respectively for creating different medical reports, and selecting at least data filter from the selection data filters on the basis of the context information.

Consequently, on the basis of the context information a suitable data filter can be selected, which then extracts the items of individual information appropriate to the medical report to be created. If, for example, a medical report on the diagnosis of a thorax scan is to be created, a corresponding data filter can be selected, which firstly identifies thorax image data in the patient data and provides it and possibly derives further items of individual information therefrom. The selection data filters can be provided, for example in a data memory of the back-end computing facility.

According to one aspect, a report type can be ascertained on the basis of the context information, with the report type indicating the type of medical report to be created, and the step of providing the data filter takes place on the basis of the ascertained report type. In other words, a data filter appropriate to the report type can be selected, therefore.

According to one aspect, the data filter has a trained function, which, on the basis of the context information, is designed to extract at least one item of individual information for generating a medical report.

A trained function generally maps input data to output data. The output data can depend in particular on one or more parameter(s) of the trained function here. The one or more parameter(s) of the trained function can be determined and/or adjusted by training. Determining and/or adjusting the one or more parameter(s) of the trained function can be based in particular on a pair of items of training input data and associated training output data, with the trained function being applied to the training input data for generating training mapping data. In particular, determining and/or adjusting can be based on a comparison of the training mapping data and the training output data. In general, a trainable function, that is to say, a function with as yet unadjusted parameters, is referred to as a trained function. In particular, the trained function can be contained in an individual filter component of the data filter. In addition, the data filter can have even further filter components, which do not comprise trained functions, because they work, for example, in a rule-based manner. Furthermore, the data filter can also have a plurality of trained functions.

Other terms for trained function are trained mapping rule, mapping rule having trained parameters, function having trained parameters, algorithm based on artificial intelligence, machine learning algorithm. One example of a trained function is an artificial neural network. Instead of the term "neural network" the term "neural net" can also be used. A neural network is basically constructed like a biological neural net—for instance, a human brain. In particular, an artificial neural network comprises an input layer and an output layer. It can also comprise a plurality of layers between input and output layers. Each layer comprises at least one, preferably a plurality of, node(s). Each node can be taken to mean a biological processing unit, for example a neuron. In other words, each neuron corresponds to an operation, which is applied to input data. Nodes of one layer can be connected to nodes of other layers by edges or connections, in particular by directed edges or connections. These edges or connections define the flow of data between the nodes of the network. The edges or connections are associated with a parameter, which is frequently referred to as "weight" or "edge weight". This parameter can regulate the importance of the task of a first node for the input of a second node, with the first node and the second node being connected by an edge. In particular, a trained function can also have a deep artificial neural network (or "deep neural network").

In particular, a neural network can be trained. In particular, training of a neural network is carried out on the basis of the training input data and the associated training output data in accordance with a "supervised" learning method, with the known training input data being input into the neural network and the output data generated by network being compared with the associated training output data. The artificial neural network learns and adjusts the edge weights for the individual nodes independently as long as the output data of the final network layer does not adequately match the training output data.

According to one aspect, at least one of the trained functions has a convolutional neural network and in particular a region-based convolutional neural network.

One technical term is convolutional neural network. In particular, the convolutional neural network can be designed as a deep convolutional neural network. The neural network has one or more convolutional layer(s) and one or more deconvolutional layer(s). In particular, the neural network can comprise a pooling layer. A neural network can be particularly efficiently used for image processing due to the use of convolutional layers and/or deconvolutional layers since, despite many connections between node layers, only a few edge weights (namely the edge weights corresponding to the values of the convolutional kernel) have to be determined. With an identical number of items of training data, the accuracy of the neural network can also be improved thereby.

One technical term is region-based convolutional neural network. The region-based convolutional neural network can have what is known as a fast region-based convolutional neural network or a faster region-based convolutional neural network. Region-based convolutional neural networks are characterized in that they have integrated functionalities for the definition of potentially relevant data regions, whereby they are suitable for identifying items of individual information in accordance with embodiments of the invention.

According to one aspect, the data filter has at least one computer linguistics algorithm, which is designed to identify and provide individual datasets in the patient data on the basis of linguistical information, in particular information containing natural speech, as individual information. In particular, the computer linguistics algorithm can be designed to evaluate metadata of individual datasets, such as headers.

According to one aspect, the data filter has a rule-based algorithm, which identifies and provides individual information on the basis of fixed selection rules.

According to one aspect, the method also comprises providing a selection of a plurality of selection templates for creating different medical reports respectively, and selecting a template from the plurality of selection templates on the basis of the context information, wherein in the step of generating, the medical report is generated on the basis of the template and in particular the at least one item of individual information is automatically input into the selected template.

Another term for template is report template. Provision and targeted selection of a suitable template can ensure that a correct medical report is created. Furthermore, improved standardization and improved comparability is possible in this way. The selection templates can be provided, for example, in a data memory of the back-end computing facility.

According to one aspect, the method also comprises providing a data structure in the back-end computing facility, which connects each selection template to one or more different data filter(s), with the step of providing the at least one data filter being based on the data structure.

The appropriate data filter can thus be automatically selected for each report template, which filter then supplies the item of individual information appropriate to the template. The data structure can be, for example, a list, which assigns a data filter to each selection template. The data structure can be saved, for example, in a data memory of the back-end computing facility. According to one embodiment, the template can be selected from the selection templates on the basis of the report type.

According to one aspect the method also comprises providing an earlier version of the medical report for the patient on the back-end computing facility, wherein the medical report is generated on the basis of the earlier version of the medical report.

The earlier version of the medical report can be provided, for example, in a data memory of the back-end computing facility (in which it was saved during generation in the back-end computing facility). Alternatively, the earlier version of the medical report can be communicated to the back-end computing facility via the medical network, for example as part of the context information or separately therefrom. Furthermore, "providing" can mean that the back-end computing facility interrogates the medical network or a storage facility incorporated therein about an earlier version of the medical report and requests it. "Is generated on the basis of the earlier version of the medical report" can comprise, for example, that the data filter is provided on the basis of the earlier version of the medical report. In particular, the same data filter as when generating the earlier version can be provided. Furthermore, "is generated on the basis of the earlier version of the medical report" can comprise that the same report template is selected as for the earlier version of the medical. Consideration of the earlier version has the advantage of coherent creation of medical reports in the medical network. The earlier version of the medical report can have already been requested in the past by the front-end computing facility or by a different front-end computing facility in the medical network.

According to one aspect, communicating the medical report to the front-end computing facility comprises communicating the earlier version of the medical report to the front-end computing facility. The user and the front-end computing facility can thereby be purposefully informed about the earlier version and can take this into account when creating a diagnosis.

According to one aspect, an item of change information can also be ascertained on the basis of a comparison between the patient data and the earlier version of the medical report, which change information indicates how at least one condition of the patient has changed since the instant of the earlier version, with the medical report also being generated on the basis of the change information and having in particular the change information for a user.

It is consequently possible to automatically ascertain how a condition of the patient has changed since the instant of the earlier medical report. The user is thus rendered capable of taking this information into account when creating the diagnosis.

According to one aspect, at least one earlier application instance of the earlier version of the medical report can also be determined in the medical network and the medical report can be communicated to the at least one earlier application instance.

The earlier application instance can be, for example, a front-end computing facility different from the front-end computing facility, a user registered in the medical network and/or a storage facility in the medical network. The earlier application instances are consequently provided with automatically updated versions of the medical report. This central version management can ensure that all instances of the medical network are working with current data.

According to one aspect, the method also comprises the steps:

ascertaining at least one missing item of individual information in the patient data on the basis of the context information and/or the data filter to be applied, and one or more of the following step(s):

communicating a note relating to the missing item of individual information to the front-end computing facility; and/or applying a data evaluation program for ascertaining the missing item of individual information from the patient data on the back-end computing facility; and/or prompting the front-end computing facility and/or a different application instance in the medical network to ascertain the missing item of individual information by way of the back-end computing facility.

A missing item of individual information can refer, for example, to a missing dataset or a missing measured value. If a dataset is missing, this can be due in particular to an examination that has not yet been performed, for instance a laboratory test or an imaging examination, of the patient. The examination has to be performed in order to generate such missing individual information. If a measured value is missing it can sometimes be extracted on the basis of the patient data. The automatic ascertainment of missing measured values means that it is systematically possible to check whether all information is available for creating the requested medical report. If not, steps can be automatically initiated, and this is conducive to quality control and unburdens the user.

According to one aspect, ascertaining the missing individual information comprises applying the provided data filter to the patient data and establishing that the patient data does not contain an item of individual information searched for with the data filter (since the result of the application of the data filter does not supply a value in this respect).

According to one aspect, applying the data evaluation program in the back-end computing facility comprises providing a plurality of selection data evaluation programs, which are respectively designed to extract different items of individual information from patient data (or to process patient data for providing corresponding individual information) and selecting the data evaluation program on the basis of the missing individual information.

The data evaluation programs can be provided, for example, in a data memory of the back-end computing facility. Items of individual information possibly already missing in the back-end computing facility can consequently be obtained, and this unburdens both the front-end computing facility as well as the user.

According to one aspect, the patient data comprises at least one medical image dataset and the missing individual information refers to a measured value to be extracted from the medical image dataset, with the data evaluation program being designed as an image processing algorithm for extracting the measured value from the medical image dataset.

According to one aspect, the method can also comprise prompting the front-end computing facility and/or a different further application instance in the medical network to apply a data evaluation program for ascertaining the missing individual information. According to one aspect, the associated data evaluation program of the front-end computing facility and/or a different further application instance can be communicated or provided by the back-end computing facility.

Further instances in the network for generating missing items of individual information can be prompted or enabled thereby. This can primarily be expedient if the raw data, to which the data evaluation program is to be applied, is not part of the provided patient data.

According to one aspect, the missing individual information refers to an examination of the patient that has not been performed, and prompting comprises prompting performance of the medical examination that has not been performed by the back-end computing facility in the medical network. In particular, a request to perform the examination can be communicated to a suitable application instance (for instance, a resource planning system or an imaging modality) in the network. In particular, the request can comprise examination parameters on the basis of which the examination can be performed. Examination parameters can comprise, for example, control parameters and/or settings of an imaging modality, etc.

According to one aspect, the method also comprises the steps:
receiving a modified medical report from the front-end computing facility on the back-end computing facility, which modified medical report is based on the medical report and compared with the medical report has one or more modification(s).

In particular, the modified medical report can have modifications made by a user. A modification can comprise, for example, an item of individual information deleted and/or modified and/or added by the user.

According to one aspect, the modified medical report can be saved in a data memory of the back-end computing facility (for example, in a report data structure for the respective patient). The modified report can thereby be centrally archived for further use and does not remain on the front-end computing facility.

According to one aspect, the data filter can also be adjusted on the basis of a comparison between the modified medical report and the medical report.

Improved data filters can be provided thereby by way of systematic evaluation of the user feedback.

According to one aspect, the method also comprises the steps:
detecting an update event in respect of the medical report on the back-end computing facility;

updating the medical report in accordance with the update event;
communicating the updated medical report to the front-end computing facility;
wherein the update event comprises in particular one or more of the following event(s):
providing updated patient data;
providing an adjusted data filter;
receiving an update request in the back-end computing facility from the medical network; and/or
expiry of a specified period since the generation of the medical report.

Once created, medical reports can be continuously kept up to date by central detection of predetermined update events and be supplied to the medical network.

According to one aspect, the method also comprises the steps:
determining at least one further application instance, different from the front-end computing facility, of the medical report in the medical network;
communicating the updated medical report to the at least one further application instance.

Application instance can refer to any instance in the medical network by which the medical report was processed. In particular, this can be a further front-end computing facility, a storage facility or also a user in the medical network. It is consequently possible to ensure that all relevant sites in the medical network receive an updated medical report.

According to one aspect, the method can also comprise an assessment of a clinical relevance of the update event, with the steps of updating and communicating only taking place if the clinical relevance lies above a threshold value.

It is consequently possible to ensure that the above-mentioned steps are only initiated if they are actually necessary, and this can save resources.

In particular, if the update event comprises providing updated patient data, the step of assessing the clinical relevance can also comprise:
applying the data filter to the updated patient data for generating at least one updated item of individual information,
comparing the updated individual information with the individual information, and
assessing the clinical relevance on the basis of the comparison of the updated individual information with the individual information, with the clinical relevance being all the greater, the greater the deviation of the updated individual information from the individual information.

On the basis of the relevant individual information it is thereby possible to decide whether an update process is to be executed, and this can possibly save resources in the medical network.

According to one aspect, the data filter is also designed to provide an item of relevance information for each individual information, which relevance information indicates a clinical relevance to the medical report to be generated.

The relevance information can be communicated together with the medical report to the front-end computing facility by the back-end computing facility. A user is consequently rendered capable of being able to assess why the corresponding items of individual information were selected for the medical report. The items of relevance information can depend in particular on the context information and/or the patient data. In particular, the relevance information can comprise a relevance value in which the relevance of an item of individual information to the medical report is quantified.

According to one aspect, the medical report is additionally generated on the basis of the relevance information. It is consequently possible to ensure, for example, that only items individual information which have adequate clinical relevance are used for the medical report. In particular, only items of individual information whose relevance value lies above a specified threshold can be used.

According to one aspect, the data filter is designed to extract a further item of individual information from the patient data for generating the medical report, wherein the further item of individual information is marked by a user on the front-end computing facility for further analysis. Furthermore, the method comprises communicating the further item of individual information and/or information relating to the further item of individual information to the front-end computing facility by the back-end computing facility for further analysis by a user.

In other words, the further item of individual information can be an item of individual information, which is relevant to the medical report, but requires further analysis by the user. The user's attention can consequently be purposefully drawn to data, which he has to analyze still further for final creation of the medical report.

According to one aspect, the further item of individual information is a dataset and in particular a medical image dataset, such as a radiology image dataset or a histopathology image dataset. Consequently, in particular such data is identified in which a human user has to carry out a further analysis. It is consequently possible to ensure that no data can be overlooked and difficult evaluation steps are simultaneously still in the hands of the user. One associated item of relevance information respectively can also be provided for further items of individual information. If the user modifies the medical report on the basis of the further items of individual information, it is possible to proceed in particular as described above and the back-end computing facility can be provided with the modified report again.

According to one aspect, the method can also comprise:
  providing a data memory in the back-end computing facility;
  storing the medical report and, optionally, the patient data, the context information, the individual information and/or the relevance information in a report data structure assigned to the patient in the data memory.

Storage in the report data structure means the medical reports can be centrally managed, and this makes improved version control possible. According to one aspect, a step of applying a report data structure to the patient can take place in the data memory.

According to one aspect, the back-end computing facility is also designed as a cloud server or cloud system.

Shared computer resources can be provided independently of device, promptly and with little effort, for example via the Internet, as a service, for instance in the form of servers, data memory or applications, by such a configuration. The back-end computing facility can be used, for example, via a browser or a suitable application on the front-end computing facility. The embodiment as a cloud consequently creates a cloud service, which can serve a large number of different front-end computing facilities, which can also belong to different medical organizations.

According to one aspect, the patient data and/or context data is provided on the back-end computing facility in anonymized and/or pseudonymized form (that is to say, the patient data and/or the context information is anonymized and/or pseudonymized). The medical report can likewise be anonymized and/or pseudonymized and/or the report data structure can be anonymized and/or pseudonymized.

According to one aspect, an apparatus for providing a medical report in a medical network having at least one front-end computing facility is provided, with the apparatus being connected to the front-end computing facility via the medical network and having a computing facility, which is designed to:
  receive an item of context information, based on a patient, from the front-end computing facility;
  provide patient data of the patient;
  provide at least one data filter on the basis of the context information, wherein the data filter is designed to extract from the patient data at least one item of individual information for generating a medical report;
  generate the medical report on the basis of the patient data and the context information by applying the data filter to the patient data; and
  communicate the medical report to the front-end computing facility.

The apparatus can be designed as the back-end computing facility.

The advantages of the proposed apparatuses substantially match the advantages of the proposed method. Features, advantages or alternative embodiments/aspects can similarly be transferred to the other claimed subject matters, and vice versa.

According to one aspect, a system for providing a medical report is also provided, which system has the above-mentioned apparatus and at least one front-end computing facility.

Furthermore, the system can have the above-mentioned data memory, for example as a central or decentral memory unit or cloud memory. Furthermore, the system can comprise one or more imaging modality(ies), such as a computed tomography system, a magnetic resonance system, an angiography system, an X-ray system, a positron emission tomography system, a mammography system, and/or a system for generating histopathology image data.

One or more example embodiments of the present invention relates to a computer program product, which comprises a program and can be directly loaded into a memory of a programmable controller and has program means, for example libraries and auxiliary functions, in order to carry out a method for providing a medical report, in particular according to said embodiments/aspects, when the computer program product is executed.

Furthermore, one or more example embodiments of the present invention relates to a computer-readable storage medium on which readable and executable program segments are saved in order to carry out all steps of a method for providing a medical report according to said embodiments/aspects when the program segments are executed by the controller.

The computer program products can comprise software having a source code, which still has to be compiled and linked or which only has to be interpreted, or an executable software code, which for execution only has to be loaded into the processing unit. The methods can be carried out quickly, in an identically repeatable manner and robustly by the computer program products. The computer program products are configured such that they can carry out the inventive method steps by means of the computing unit. In each case the computing unit has to have the requirements, such as an appropriate main memory, an appropriate processor, an appropriate graphics card or an appropriate logic unit, so the respective method steps can be efficiently carried out.

The computer program products are saved, for example, on a computer-readable storage medium or stored on a network or server, from where they can be loaded into the processor of the respective computing unit, which can be directly connected to the computing unit or can be designed as part of the computing unit. Furthermore, control information of the computer program products can be saved on a computer-readable storage medium. The control information of the computer-readable storage medium can be designed in such a way that it carries out an inventive method when the data carrier is used in a computing unit. Examples of computer-readable storage medium are a DVD, a magnetic tape or a USB stick on which electronically readable control information, in particular software, is saved. When this control information is read from the data carrier and saved in a computing unit, all inventive embodiments/aspects of the previously described method can be carried out. One or more example embodiments of the present invention can thus also start from said computer-readable medium and/or said computer-readable storage medium. The advantages of the proposed computer program products or the associated computer-readable media substantially match the advantages of the proposed methods.

FIG. 1 represents a system 1 for providing a medical report MB according to one embodiment. The system 1 has at least one front-end computing facility 50, one storage facility 60 and one back-end computing facility 200, which have a communication link to each other over a medical network 10.

The front-end computing facility 50 can be designed, for example, as a diagnostic station or diagnostic workstation at which a user can screen and analyze patient data PD as well as create, check, change and appraise medical reports MB. For this, the front-end computing facility 50 can have a user interface (not represented). The front-end computing facility 50 can have a processor. The processor can have a Central Processing Unit (CPU), a Graphics Processing Unit (GPU), a digital signal processor (DSP), an image processing processor, an integrated (digital or analog) circuit or combinations of said components and further facilities for providing a medical report MB according to embodiments. The front-end computing facility 50 can comprise, for example, a desktop PC, laptop or a tablet.

The front-end computing facility 50 can be provided with the patient data PD from the storage facility 60 via suitable interfaces. Typically, a system as shown in FIG. 1 has a plurality of front-end computing facilities 50, which all access the same storage facilities 60. In the embodiment shown, the storage facility 60 and the front-end computing facility(ies) 50 are part of the same medical organization ORG. A medical organization ORG can be, for example, a practice, a group of practices, a hospital or a group of hospitals. In the embodiment shown, the back-end computing facility 200 is also part of the medical organization ORG, moreover. Accordingly, the medical network 10 can be designed as an internal network of this organization ORG and comprise, for example, an Intranet (for instance, a Local Area Network and/or a Wireless Local Area Network).

The storage facility 60 can be designed as a central or decentral database. The storage facility 60 can in particular be part of a server system. The storage facility 60 can in particular be part of a medical information system such as a hospital information system (HIS), a PACS system, a laboratory information system (LIS), an "electronic medical record" (EMR) information system and/or further medical information systems. The storage facility 60 is designed to save a number of items of patient data PD. The storage facility 60 can also be referred to as a data source or database.

An item of individual information EI can be an individual, in particular self-contained, dataset, measured value or medical diagnosis contained in the patient data PD.

The patient data PD and/or the individual information EI can have medical image data and/or other medical data that does not comprise image information. Image data can refer in this connection to medical image data having two or three spatial dimensions. Furthermore, the image data can also have a time dimension. The image data can have been generated, for example, with an imaging medical modality, such as an X-ray, computed tomography, magnetic resonance, positron emission tomography or angiography device or further devices. Such image data can also be referred to as radiology image data.

Furthermore, patient data PD and/or the individual information EI can also comprise histopathology image data, which shows one or more histopathology image(s) respectively. Histopathology image data is image data, which is based on a tissue sample of a patient. Tissue sections are prepared from the tissue sample and are dyed with a histological dye. The tissue sections prepared in this way are then digitized to obtain the histopathology image data. Specialized scanners, what are known as slide scanners, can be used for this. The image recorded in the process is also referred to as a "whole slide image". The image data recorded in the process is typically two-dimensional pixel data.

The image data contained in the patient data PD and/or in the individual information EI can be formatted in accordance with the DICOM format, for example. DICOM (=Digital Imaging and Communications in Medicine) is an open standard for the communication and administration of medical image data and associated data.

In addition to image data, the patient data PD and/or the individual information EI can also comprise non-image data. Non-image data can be, for example, examination results, which are not based on medical imaging. This can comprise laboratory data, vital data, spirometry data or the protocols of neurological examinations. In addition, non-image data can comprise text datasets, such as structured and unstructured medical diagnoses or medical reports. Non-image data can also be patient-based data, moreover. This can comprise, for example, demographic details relating to the patient, for instance relating to their age, sex or body weight. The non-image data can be incorporated in the image data as metadata, for example. Alternatively or in addition, the non-image data can also be saved in an electronic medical record (or EMR for short) of the patient, that is to say, separately from the image data. Such electronic medical records can be archived in the storage facility 60, for example.

The back-end computing facility 200 can have a processor. The processor can have a Central Processing Unit (CPU), a Graphics Processing Unit (GPU), a digital signal processor (DSP), an image processing processor, an integrated (digital or analog) circuit or combinations of said components and further facilities for providing a medical report MB according to embodiments. The back-end computing facility 200 can be implemented as individual components or have a group of computers, such as a cluster. A system of this kind can be called a server system. Depending on the embodiment, the computing unit 20 can as a local server. Furthermore, the computing unit 20 can have a main memory, such as a RAM, in order to temporarily store, for example the patient data PD, data filters DF, items of individual information EI, or report templates BT. The back-end computing facility 200 is designed, for example by way of computer-readable instructions, by design and/or hardware, in such a way that it can carry out one or more method step(s) according to embodiments of the present invention.

The back-end computing facility 200 can have a data memory 210, which is designed to centrally store patient data PD, data filters DF, report templates BT, etc. for a plurality of different patients. In particular, the data memory 210 can be designed to store this information in a dedicated report data structure BDS. The report data structure BDS can be designed in such a way that a plurality of patients and different versions of a medical report MB can be managed in the data memory 210.

The back-end computing facility 200 can be connected to the front-end computing facility 50 and or the storage facility 60 via suitable interfaces. Via this interface the back-end computing facility 200 can receive patient data PD and context information KI, on the basis of which a medical report MB is to be created with which the front-end computing facility 50 is to be provided.

The context information KI indicates the boundary conditions under which a medical report MB is to be created. This can be, for example, a diagnosis task, a type of requested medical report MB, a stage of the patient, a type of examination, on the basis of which the medical report MB is to be created and the like.

The back-end computing facility 200 can have different modules available for providing a medical report MB. A first module 220 can be designed as a data filter module. The data filter module 220 can be designed in particular to provide, on the basis of the context information KI and/or the patient data PD, a data filter DF, which is suitable for identifying and providing individual information EI contained in the patient data PD, which is required for a medical report MB to be communicated. In particular, the data filter module 220 can be designed to select from a plurality of selection data filters DF one or more suitable data filter(s) DF and/or to appropriately adjust a data filter DF.

A further module 230 can be designed as a relevance module. The relevance module 230 can be designed to provide relevance information RI relating to individual information EI. The relevance information RI can comprise a value or a detail about how relevant the associated individual information EI is to the medical report MB to be created. The relevance module 230 can be designed in particular to provide the relevance information RI on the basis of the context information KI. By way of example, an item of relevance information RI for thorax scans U1 of a patient, for example, can be derived by the relevance module 230 as follows. If, for example, the lungs are being diagnosed, it is possible to firstly look in the patient data PD for lesions in the lungs (for instance, using the data filter module 220). If a diagnosis is identified as the L1 pulmonary nodule, for example in accordance with a specified clinical ontology (for example, "RID50149, RADLEX, Pulmonary nodule"), the diagnosis can thus be assigned a lower relevance value as relevance information RI than if the diagnosis was identified as a L4 pulmonary nodule. During the subsequent provision of the medical report MB it is then possible to dispense with a scan of the L1 pulmonary nodule in the medical report MB. The relevance module 230 can also be designed to save the respective relevance information RI in connection with the respective individual information EI, for example in the report data structure BDS.

A further module 240 can be designed as a checking module which is designed to check the patient data PD (in particular on the basis of the context information KI) for coherency and completeness. During the check for coherence it is possible to check, for example, whether the clinical status of the patient corresponds to the specifications. For this, it is possible to check, for example, whether the patient data PD reflects the clinical steps or examinations U1, U2, U3, expected for the patient in accordance with the context data KD, in the correct order and whether items of individual information EI are erroneous. The check for completeness can comprise, for example, a check as to whether items of individual information EI are missing, based on the clinical status of the patient.

A further module 250 can be designed as a correlation module, which is designed to map items of individual information EI on each other, which items originated at different instants, in order to decide, for example, whether updated patient data PD contains an updated item of individual information EI or a completely new item of individual information EI. For this, the correlation module can apply, for example, a data filter DF to updated patient data PD and compare the items of individual information EI identified by the data filter DF with items of individual information EI stored in the report data structure BDS.

A further module 260 can be designed as an update module. The update module can be designed in particular to update an existing medical report MB and to provide the relevant front-end computing facilities 50 and further application instances in the medical network 10 with the updated medical report MB.

Finally, a further module 270 can be designed as a storage module, which saves the information used and generated in the provision of the medical report MB in the data memory 210 in a specified report data structure BDS.

The undertaken division of the back-end computing facility 200 into modules 220-270 is solely for simpler explanation of the mode of operation of the back-end computing facility 200 and should not be understood as being limiting. The modules 220-260 or their functions can also be combined in one element. The modules 220-260 can be conceived in particular also as computer program products or computer program segments, which implement one or more of the method step(s) described below when executed in the back-end computing facility 200.

In the embodiment shown in FIG. 1, the back-end computing facility 200 is part of the medical organization ORG. In other words, the back-end computing facility 200 can be conceived as a central service facility for providing and managing medical reports MB. For example, the back-end computing facility 200 is implemented in the medical organization ORG "on premises", for example as a server system. Alternatively, the back-end computing facility 200 can also be implemented as a server system outside of the medical organization ORG.

Figure 2:
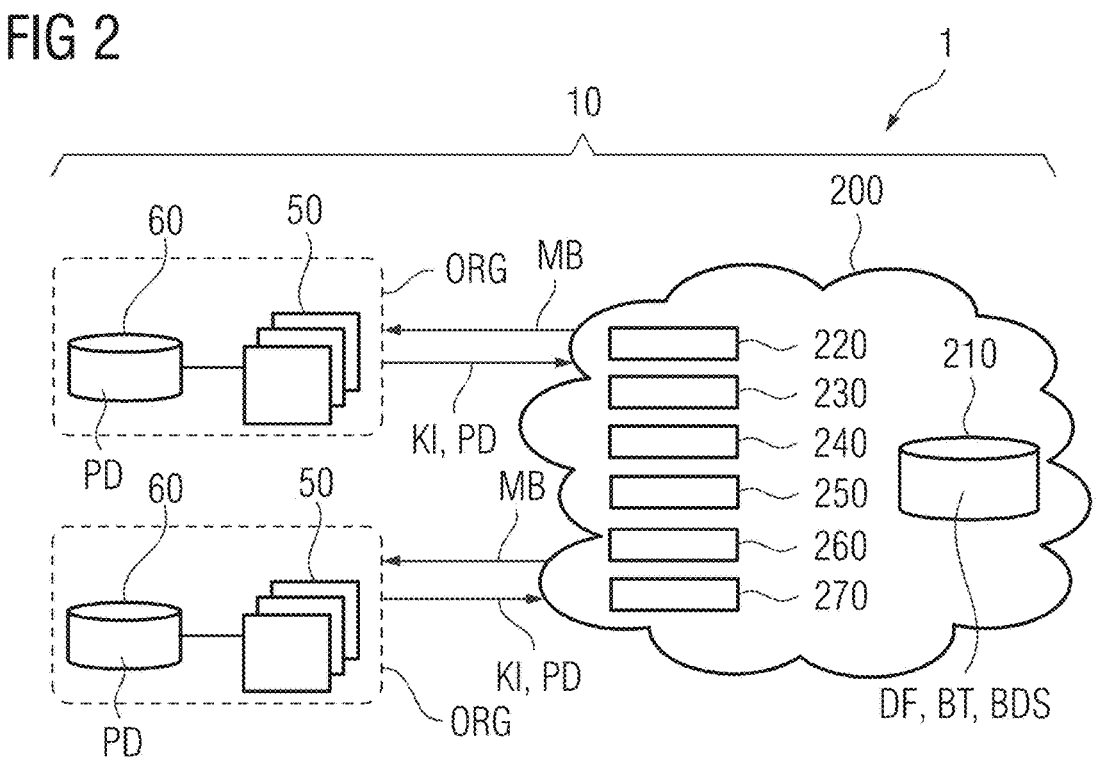
FIG. 2 shows a schematic representation of an embodiment of a system for providing a medical report according to a further embodiment.

FIG. 2 represents a further embodiment of the one system 1 for providing a medical report MB. Identical reference characters to those in FIG. 1 designate identical or functionally identical components.

In contrast to the embodiment shown in FIG. 1, the back-end computing facility 200 is configured as a cloud-based computing facility or cloud server. In this embodiment, the back-end computing facility 200 is thus generally not part of a medical organization ORG in which the patient data PD is stored and in which the front-end computing facilities 50 are arranged. In other words, the back-end computing facility 200 can be available to a plurality of medical organizations ORG as a service facility for providing and managing medical reports MB. The back-end computing facility 200 according to this embodiment is preferably designed as a cloud server. The back-end computing facility can have in particular a real or virtual group of computers and/or storage facilities. Depending on the embodiment, the computing unit 20 can be designed as a local server or as a cloud server. The back-end computing facility 200 can make shared computer resources available as a service, for instance in the form of servers, data memory or applications for providing a medical report MB, to the medical organizations ORG or the front-end computing facilities. The computer resources of the back-end computing facility 200 can be used by the medical organization ORG or the front-end computing facility 50, for example via a program interface (API) or application loaded for the user via a website or in the front-end computing facility 500.

In this embodiment, the back-end computing facility 200 can have a communications link to the medical organization ORG or the front-end computing facilities 50 and/or data memory 60 of the medical organization ORG, for example via the Internet. Patient data PD and/or context information KI can be transferred to the back-end computing facility 200 by the medical organization ORG in anonymized and/or pseudonymized form. Conversely, a medical report MB can be transferred by the back-end computing facility 200 to the medical organization ORG, likewise in anonymized and/or pseudonymized form.

Figure 3:
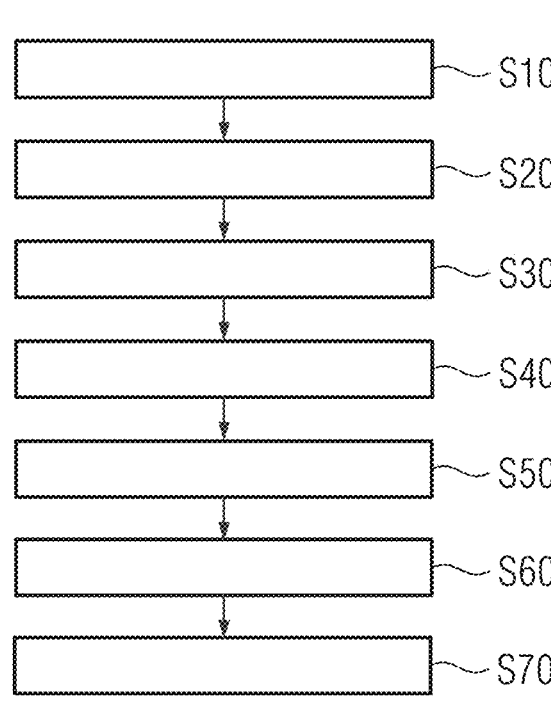
FIG. 3 shows a flowchart of a method for providing a medical report according to one embodiment.

FIG. 3 represents a schematic flowchart of a method for providing a medical diagnosis MB. The order of the method steps is limited neither by the represented sequence nor by the chosen numbering. The order of the steps can thus possibly be interchanged and individual steps can be omitted. In addition, one or more step(s), in particular a sequence of steps, and optionally the entire method, can be carried out repeatedly.

In a first step S10, the context information KI is received in the back-end computing facility 200. The context information KI can be communicated to the back-end computing facility 200 by the one of the front-end computing facilities 50. The context information KI comprises a context for a medical report MB to be created for a specific patient by a specific user of the front-end computing facility 50. The context information KI can be user- and/or patient-specific. For example, the context information can comprise an electronic user identifier, which uniquely identifies the user in the medical network 10. In addition or alternatively, the context information KI can comprise an electronic patient identifier, which uniquely identifies the patient in the medical network 10. User and/or patient identifiers can comprise, for example, the name of the user or patient. Alternatively, user and/or patient identifiers can be anonymized or pseudonymized.

Furthermore, the context information KI can have a medical context in which the medical report MB is to be created. This can be, for example, a diagnosis task, which the user is to complete using patient data on the front-end computing facility 50. In addition or alternatively, the context information can comprise a detail of a clinical stage of the patient. For example, the context information can comprise a detail that a particular examination U1, U2, U3 and/or treatment U1, U2, U3 of the patient has finished. In addition or alternatively, the context information KI can comprise a detail of a disease or diagnosis of the patient. In addition or alternatively, the context information KI can comprise a detail of an organization ORG to which the front-end computing facility 50 belongs. The context information KI can also comprise a request to provide a medical report MB.

In a further step S20, patient data PD of the patient is provided in the back-end computing facility 200. The patient data PD can be communicated to the back-end computing facility 200 by the front-end computing facility 50, for example together with or as part of the context information KI. In addition or alternatively, the back-end computing facility 200 can retrieve patient data PD from the storage facility 60 or from a data memory 210 incorporated in the back-end computing facility 200. This can take place on the basis of a patient identifier contained in the context information KI. In particular, the patient data PD can also comprise earlier instances of a medical report MB of the patient.

In an optional step S30, one or more report template(s) BT can then be selected for creating the medical report MB. The report template BT to be used can depend, for example, on the type of disease of the patient, the clinical stage of the patient, a preferred report template of the user, specifications of an organization ORG to which the front-end computing facility belongs, relevant medical guidelines, already existing, earlier medical reports medical examinations U1, U2, U3 that have been performed, the type of patient data PD, etc. Accordingly, one or more report template(s) BT can be provided in step S30 on the basis of the context information KI and/or the patient data PD. In particular, step S30 can comprise keeping ready a plurality of selection report templates, for example in the data memory 210 of the back-end computing facility 200, from which the report template BT to be used is then selected on the basis of the context information KI and/or the patient data PD. In some exemplary embodiments a medical guideline can also be identified on the basis of the patient data PD and/or the context information KI, and the report template BT can be selected on the basis of the identified medical guideline. The report templates BT are not necessarily to be regarded as self-contained templates, rather individual report templates BT can be combined in a modular fashion to provide the medical report MB.

In a next step S40, a data filter DF is provided to extract, from the patient data PD, one or more item(s) of individual information EI, which are relevant to the medical report MB to be created.

Figure 4:
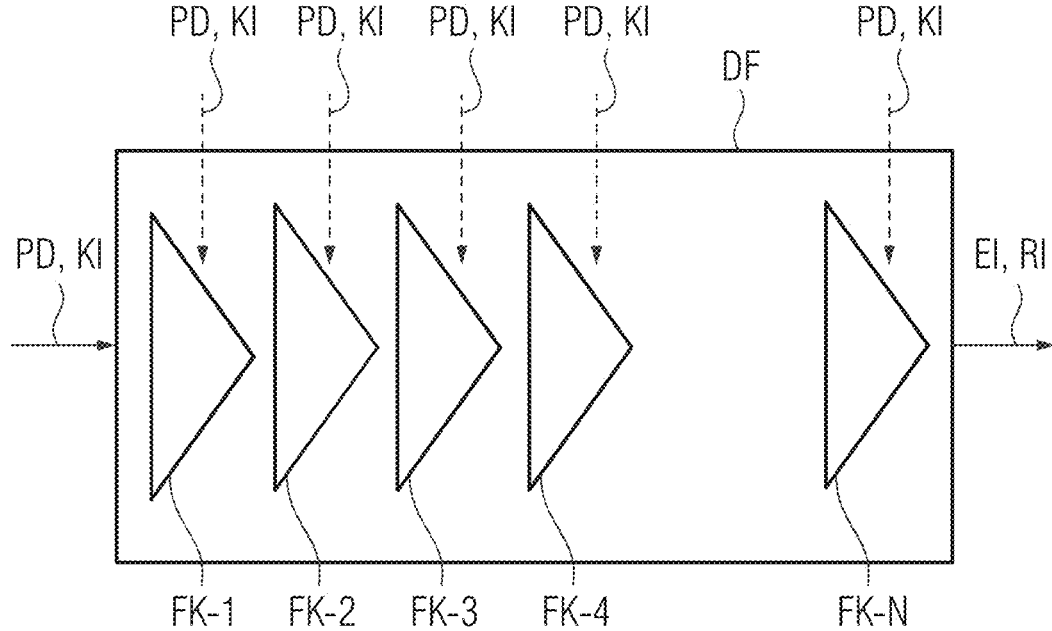
FIG. 4 shows an implementation of a data filter for providing a medical diagnosis from patient data according to one embodiment.

The data filter DF can comprise a plurality of filter components FK-1, FK-2, . . . , FK-N, which are configured in particular adaptively and can be arbitrarily combined with each other. FIG. 4 shows an exemplary embodiment of the data filter DF.

For example, the data filter DF can comprise a temporal filter component FK-1, which is designed to filter from the patient data PD those datasets which are relevant to the medical report MB to be created. Information that lies too far in the past, for example, can thus be discarded. The temporal filter component can be configured in particular adaptively and be adjusted on the basis of the context information KI and/or the patient data PD and/or an identified medical guideline and/or the clinical status of the patient.

Furthermore, a data type filter component FK-2 can be incorporated, which is designed to filter out from the entirety of the patient data PD the type of data which is relevant to the medical report to be created. If, for example, a radiological diagnosis is to be made, the data type filters can firstly identify radiology image data. The data type filter component FK-2 can be based, for example, on one or more medical guideline(s), which specify a data type for a particular item of context information KI.

Furthermore, the data filter DF can incorporate an anatomy filter component FK-3, which is designed to identify and provide those datasets in the patient data PD which relate to an anatomical region of the patient to be considered in the medical report MB. If, for example, a prostate of a patient is to be diagnosed, medical image data showing the prostate and biopsy data of the prostate can thus be identified.

Furthermore, the data filter DF can incorporate a version filter component FK-4, which is designed to identify and provide earlier medical reports or earlier versions of the medical report MB in the patient data PD. Thus it is possible to purposefully search for what are known as DICOM Structured Reports (DICOM-SR), for example, which already exist for the patient from earlier diagnoses.

Further filter components are conceivable apart from said filter components FK-1, FK-2, FK-3, FK-4. For example, a filter component (not represented separately) can be designed to map particular user preferences. Thus, for example, user profiles for different users within the medical network 10 can be saved in the back-end computing facility 200, for example in the data memory 210, which profiles can be retrieved, for example, on the basis of a user identifier. If it emerges therefrom, for example, that the user of the front-end computing facility 50 purposefully preferably takes into account certain slices of a CT image dataset when creating a medical report MB and/or incorporates mappings therefrom in the medical report, such slices can be identified in the patient data PD and be provided. Furthermore, a further filter component (not represented separately) can be designed to take into account particular needs or specifications of the organization ORG to which the front-end computing facility 50 belongs when creating the medical report MB. For example, profiles for different organizations ORG within the medical network 10 can be saved in the data memory 210 of the back-end computing facility, which profiles can be retrieved on the basis of the context information KI. On the basis of the profile thus retrieved, the data filter DF or the filter component can identify and provide from the patient data PD items of individual information or datasets, which match in particular the needs or specifications of the organization ORG to which the front-end computing facility 50 belongs.

Furthermore, the data filter DF can incorporate a relevance filter component FK-N, which is designed to check items of individual information contained in the patient data PD as to whether they should be taken into account when providing the medical report MB. For example, the filter component KF-N can extract an item of individual information EI from the patient data PD for this purpose and check its relevance. In particular, the relevance filter component FK-N can be designed to determine a corresponding item of relevance information RI for an item of individual information EI. For this, the item of individual information EI can be compared, for example, with a specified threshold value. The threshold value can be specified, for example, by a medical guideline. In addition, the filter component FK-N and therewith the data filter DF can be designed to compare the extracted item of individual information EI with a corresponding item of individual information EI from an earlier instant. As a function of the comparison it is then possible to decide whether a relevance condition is met. Thus, for example, an organ volume can be extracted at different instants from the patient data PD as an item of individual information EI. If the comparison points toward a pathological organ enlargement, the relevance filter component FK-N can provide an item of relevance information RI showing this accordingly. Alternatively, an item of individual information EI can also be compared (preferably semantically) with a clinical ontology (for example, SNOMED or RADLEX) to arrive at an item of relevance information RI. Thus, for example, an L1 pulmonary nodule can have less relevance than an L4 pulmonary nodule. Further classification algorithms can also be implemented, moreover, to provide a corresponding item of relevance information RI relating to an item of individual information EI.

Provision of the data filter DF in step S40 can mean in particular that the data filter DF is adjusted or adapted on the basis of the context information KI and/or the patient data PD. In particular, individual filter components KF-1, KF-2, KF-3, . . . , KF-N can be selected and/or adjusted for this on the basis of the context information KI and/or the patient data PD. Thus, for example, filter parameters such as the data types, time periods or threshold values to be considered can be selectively adjusted as a function of the respective circumstance of the individual case. Alternatively or in addition, various and/or differently pre-configured data filter DFs can be saved, for example, in the data memory 210 of the back-end computing facility 200 for selection as the selection data filter. On the basis of the context information KI and/or the patient data PD, a data filter DF can then optionally be provided in step S40 by selection of a data filter DF (to be used) from the selection data filters on the basis of the context information KI and/or the patient data PD. A data filter DF (to be used) can optionally be selected from the selection data filters additionally or alternatively on the basis of a medical guideline.

In an optional embodiment, a data structure can also be provided in the back-end computing facility 200, which associates a report template BT with an associated data filter DF. A suitable data filter DF can thus be provided on the basis of the data structure and a report template BT already selected. Provision can comprise a selection and/or adjustment of individual filter components FK-1, FK-2, FK-3, . . . , FK-N. Alternatively or in addition, provision can comprise selecting a data filter DF from a plurality of selection data filters on the basis of the data structure and the report template BT. The data structure can be, for example, a type of electronic assignment table, which links different filter parameters and/or filter components FK-1, FK-2, FK-3, . . . , FK-N and/or data filters DF to different report templates BT.

A medical report MB is provided in step S50. For this, for example, the provided data filter DF can be applied to the patient data PD. The data filter DF can extract at least one item of individual information EI from the patient data PD and provide it for the medical report MD. In particular, provision in step S50 can comprise inputting the individual information EI into a report template BT. In particular, at least one item of individual information EI can be input into a location of a report template BT provided for this. In other words, the report template BT can be at least partially filled in step S50. The provided medical report MD can be completed. Alternatively, the provided medical report MD can be provided for further processing on the front-end computing facility 50. In particular, the medical report MD can be provided by the back-end computing facility 200 in anonymized and/or pseudonymized form. Such an anonymized and/or pseudonymized medical report MD can then be de-anonymized and/or de-pseudonymized as required on the front-end computing facility 50.

In step S60, the medical report MD provided in step S50 is communicated to the front-end computing facility 50.

In the optional step S70, the medical report MB is saved in the data memory 210 of the back-end computing facility 200. The patient data PD, the data filter DF used and the context information KI can likewise be saved in the data memory 210. In particular, the medical report MB and/or the patient data PD and/or the data filter DF can be saved in such a way that they are linked to the context information KI. In other words, a report data structure BDS of the patient can thus be saved and maintained in the back-end computing facility 200, which structure can be accessed repeatedly for creating medical reports MB. In particular, the report data structure BDS thus saved in the data memory 210 can be regarded as a type of virtual medical report relating to a patient. The central provision of this report data structure BDS in a back-end computing facility 200 allows this virtual medical report to be transferred at any time and as a function of the respective context information KI into a "concrete" medical report MB, with which the front-end computing facility 50 can then be provided. The patient data PD as an input variable is linked via the data filters DF to the provided medical reports MB as an output variable in the report data structure BDS thus created. Furthermore, the report data structure BDS links different versions of medical reports MB of the patient via the data filters DF. User information can also be saved in the report data structure BDS, which information indicates which application instances (for example, which front-end computing facilities or which users) within the medical network 10 use a respective provided medical report MB and/or a copy hereof or access it. For this, the medical network can be designed such that the back-end computing facility 200 is provided with appropriate user information whenever an application instance accesses a medical report MB.

Figure 5:
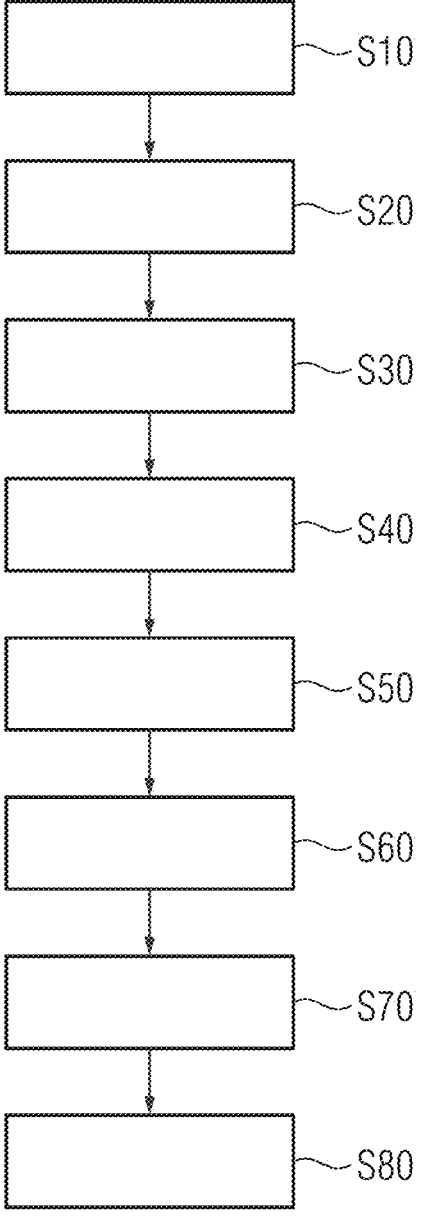
FIG. 5 shows a flowchart of a method for providing a medical report according to one embodiment.

FIG. 5 represents a schematic flowchart of a method for providing a medical report MB according to a further embodiment. The order of the method steps is limited neither by the represented sequence nor by the chosen numbering. The order of the steps can thus possibly be interchanged and individual steps can be omitted. In addition, one or more step(s), in particular a sequence of steps, and optionally the entire method, can be carried out repeatedly. Method steps which are provided with identical reference characters compared to FIG. 3 match the steps already described in connection with FIG. 3. The method steps additionally described in FIG. 5 can be combined with the other methods described herein.

In the embodiment shown in FIG. 5, an earlier version of the medical report MB for the patient is provided in step S25 in the back-end computing facility 200. The earlier version of the medical report MB can be in particular a medical report MB, which was generated with an identical or at least similar data filter DF and/or on the basis of an identical and/or at least similar report template BT and/or on the basis of an identical and/or at least similar item of context information KI. The earlier version of the medical report MB can be provided, for example, as part of the patient data PD, which is either saved in the data memory 210 of the back-end computing facility 200, for example in the above-mentioned report data structure BDS, or is communicated to the back-end computing facility 200, for example with the context data KI. An earlier version of the medical report MB can be retrieved, for example, from the data memory 210 on the basis of the context information KI. The context information KI assigned to the earlier version of the medical report MB, report templates BT, items of individual information EI, items of relevance information RI and data filters DF can possibly be retrieved from the report data structures BDS saved in the data memory 210.

The steps S30, S40 and S50 can then optionally be carried out additionally on the basis of the earlier version of the medical report MB. For example, the report template BT can be selected on the basis of the earlier medical report. In particular, the same report template BT as in the earlier version of the medical report MB can be selected. Furthermore, the data filter DF can be selected on the basis of the earlier medical report. In particular, the same data filter DF as in the earlier version of the medical report MB can be selected.

In the optional step S55, an item of change information is then additionally ascertained in the embodiment shown in FIG. 5, and this indicates how a medical report MB ascertained in step S50 differs from the earlier version of the medical report MB. For this, for example, an item of individual information EI extracted from the patient data PD for providing the medical report MB can be compared with the corresponding item of individual information EI of the earlier medical report.

In step S60, the item of change information can then be communicated together with the medical report MB to the front-end computing facility 50. Furthermore, the item of change information in step S70 can be saved in the report data structure BDS in the data memory 210.

In addition, the medical report MB can be communicated in the optional step S80 to the application instances within the medical network 10 in which access was made to the earlier version of the medical report MB (also earlier application instance). An application instance can be, for example, a further front-end computing facility 50 or a user. Earlier application instances can be ascertained, for example, on the basis of an item of application information in which the accesses to the earlier version of the medical report MB are "logged". In addition or alternatively, the change information can be communicated to the application instances. In one exemplary embodiment, an assessment of relevance can precede communication the application instances, for example. Correspondingly, step S80 can have an optional sub-step of assessing the relevance of the change information. This can have, for example, a check as to whether the change information overshoots a threshold value. Communication to the application instance(s) can take place or not take place as a function of the assessment step. For example, the medical report MB and/or the change information can only be communicated when the change information overshoots the threshold value.

Figure 6:
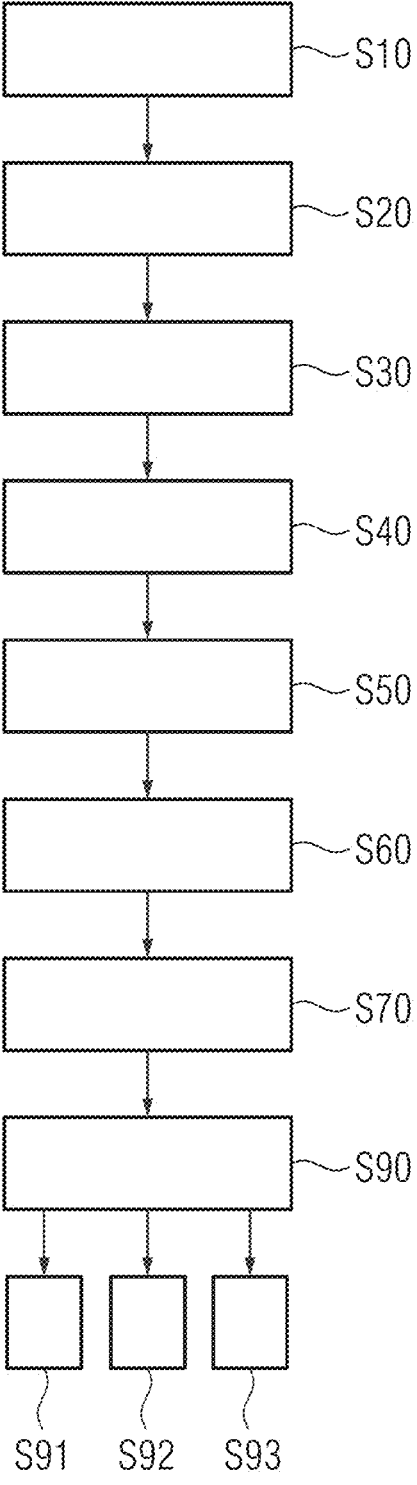
FIG. 6 shows a flowchart of a method for providing a medical report according to one embodiment.

FIG. 6 represents a schematic flowchart of a method for providing a medical diagnosis MB according to a further embodiment. The order of the method steps is limited neither by the represented sequence nor by the chosen numbering. The order of the steps can thus possibly be interchanged and individual steps can be omitted. In addition, one or more step(s), in particular a sequence of steps, and optionally the entire method, can be carried out repeatedly. Method steps which are provided with identical reference characters compared to FIG. 3 match the steps already described in connection with FIG. 3. The method steps additionally described in FIG. 6 can be combined with the other methods described herein.

In step S45, the patient data PD is verified or checked for integrity in the exemplary embodiment shown in FIG. 6, in particular with regard to the medical report MB to be created. In particular, an item of missing or incorrect individual information EI in the patient data PD can be ascertained.

A missing or an incorrect item of individual information EI can refer, for example, to a missing or incorrect measured value, a medical examination U1, U2, U3 that has not been performed, missing or incorrect datasets in the patient data, etc. In other words, a check is thus made as to whether the clinical status of the patient is coherent.

A missing or an incorrect item of individual information EI can be ascertained, for example, by applying the data filter DF to the patient data PD. If, for example, applying the data filter DF does not supply the at least one item of individual information EI, then this information is missing in the patient data PD, and the medical report MB to be created using the context information KI cannot be generated. If the at least one item of individual information EI being sought is contained in the patient data PD, it can be provided by applying the data filter DF. This item of individual information EI can then be subjected to a plausibility check in step S45. For this, the item of individual information EI can be compared, for example, with specified limit values or an item of change information (see description of FIG. 5) can be evaluated. Alternatively, a missing or an incorrect item of individual information EI can be acquired by comparison with a pertinent medical guideline.

If a missing or an incorrect item of individual information EI is established in step S45, it is possible to circumvent this in a different way in step S90. Firstly, a communication about the missing or incorrect item of individual information EI can be communicated to the front-end computing facility 50 (optional sub-step S91), so the necessary steps are initiated there. Secondly, the information about the missing or incorrect item of individual information can be saved in the report data structure BDS of the data memory 210.

Furthermore, steps can be initiated to correct the missing or incorrect item of individual information EI. In an optional sub-step S92, a data evaluation algorithm can be selected, for example, on the back-end computing facility 200, which algorithm is configured to automatically carry out a data evaluation on the basis of the patient data PD in order to provide a specified item of individual information EI. For example, a data evaluation algorithm of this kind can be implemented as an image data evaluation algorithm, which is configured to extract measured values from medical image data. In some exemplary embodiments, different selection data evaluation algorithms can be provided in the back-end computing facility 200, from which a suitable data evaluation algorithm for providing the missing item of individual information EI or for correcting the incorrect item of individual information can then be selected.

Alternatively, the front-end computing facility 50 or a different application instance in the medical network 10 can be prompted by the back-end computing facility 200 to provide the missing item of individual information (optional sub-step S93). For example, the back-end computing facility 200 can actuate the front-end computing facility 50 or another application instance in such a way that a suitable data evaluation algorithm is applied to locally available patient data in order to provide the missing item of individual information EI. If the missing item of individual information EI refers to an examination U1, U2, U3 that has not been performed, the front-end computing facility 50 or another application instance can be actuated in such a way that the examination U1, U2, U3 that has not been performed is initiated for the patient. For example, a corresponding task can be input into an examination planning system. Such an examination planning system can control, for example, the occupation of imaging modalities such as CT or MR devices in a medical network 10. Consequently, an examination of the patient can be directly prompted in the medical network 10 for generating the item of missing individual information EI. Advantageously, suitable examination parameters can be communicated by the back-end computing facility 200. For example, such examination parameters can refer to an anatomical region of the patient, which is to be examined by way of imaging, or comprise imaging parameters, such as an MR sequence to be used and the like. Similarly, appropriate tissue sections and/or suitable histopathological dyes can be prompted, for instance in a digital pathology workflow.

Figure 7:
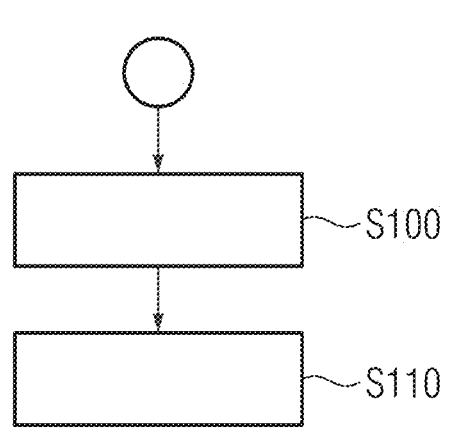
FIG. 7 shows a flowchart of a method for providing a medical report according to one embodiment.

FIG. 7 represents a schematic flowchart of a method for providing a medical diagnosis MB according to a further embodiment. The order of the method steps is limited neither by the represented sequence nor by the chosen numbering. The order of the steps can thus possibly be interchanged and individual steps can be omitted. In addition, one or more step(s), in particular a sequence of steps, and optionally the entire method, can be carried out repeatedly. Method steps which are provided with identical reference characters compared to FIG. 3 match the steps already described in connection with FIG. 3. The method steps additionally described in FIG. 7 can be combined with the other methods described herein.

Building on one or more of said method(s), a modified medical report MB can be communicated in step S100 to the back-end computing facility 200 by the front-end computing facility 50 in the method shown in FIG. 7. The modified medical report MB is based on the medical report MB communicated in step S60 and has one or more modification(s) compared with it. Such modifications can comprise, for example, changes to the communicated medical report MB by the user, such as corrections, deletions or additions.

The embodiment shown in FIG. 7 provides utilizing this information to improve the data filter DF used. For this, it is provided in step S110 that the data filter DF is adapted on the basis of a comparison between the modified medical report MB and the communicated medical report MB. Consequently, for example, filter components FK-1, FK-2, FK-3, . . . , FK-N can be supplemented or adapted.

Figure 8:
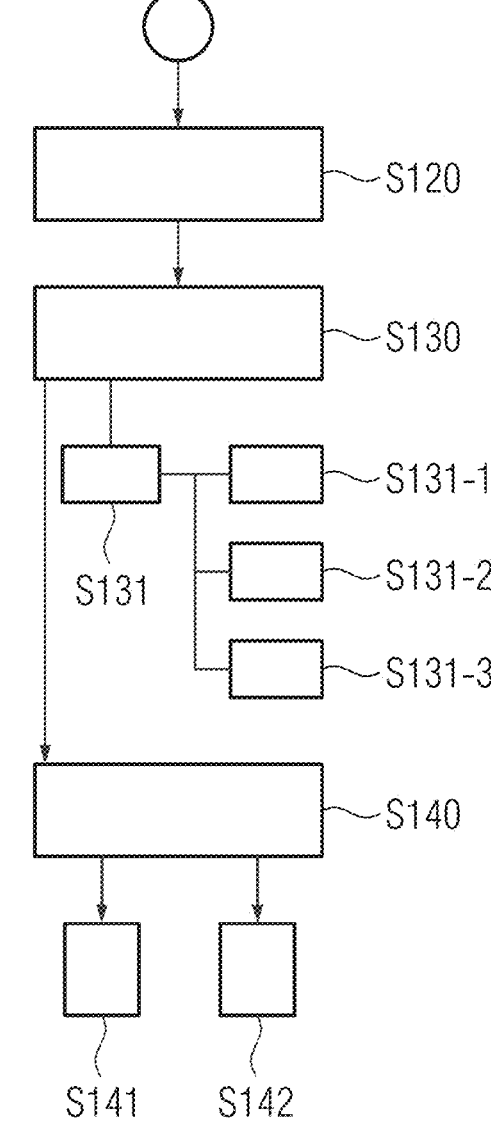
FIG. 8 shows a flowchart of a method for providing a medical report according to one embodiment.

FIG. 8 represents a schematic flowchart of a method for providing a medical diagnosis MB according to a further embodiment. The order of the method steps is limited neither by the represented sequence nor by the chosen numbering. The order of the steps can thus possibly be interchanged and individual steps can be omitted. In addition, one or more step(s), in particular a sequence of steps, and optionally the entire method, can be carried out repeatedly. Method steps which are provided with identical reference characters compared to FIG. 3 match the steps already described in connection with FIG. 3. The method steps additionally described in FIG. 8 can be combined with the other methods described herein.

In step S120, firstly an update event in respect of one or more medical report(s) MB generated in the back-end computing facility 50 is/are detected. An update event can be any event in the medical network which requires reconsideration of the generated medical reports. Such an update event can be given, for example, in that new patient data PD exists for a patient. Furthermore, an update event can be given in that one or more data filter(s) DF were adjusted. This can occur, for example, by way of the method described in connection with FIG. 7 or result from amended medical guidelines. Furthermore, an update event can comprise changed requirements for the creation of medical reports MB of a front-end computing facility 50 or an associated medical organization ORG. In addition, an update event can comprise an expiry of a specified period since communicating or providing the medical report MB or a request to update a communicated medical report MB. Detection of such update events makes it possible to automatically detect whether medical reports communicated in the past have to be updated and possibly provided afresh.

The medical report MB is updated on the back-end computing facility 200 in step S130. The medical report MB can be adapted in accordance with the update event. For example, the patient data PD can be re-evaluated with an adjusted data filter DF, or updated patient data PD can be evaluated with the data filter DF, which was already used for the medical report MB, or both. In addition or alternatively, (for example, by taking into account modified medical guidelines) different data filters DF than during provision of the medical report MB can be selected and applied to the patient data PD.

It is optionally possible to assess the relevance in step S130 as to whether the updated medical report MB contains changes, which are so significant that a transmission of the medical report MB is justified (optional sub-step S131). For this, in general the updated medical report MB can be compared with the medical report MB and the changes can be evaluated on the basis of the comparison. If, for example, the update event comprises providing updated patient data PD, the assessment of relevance in sub-step S131 can comprise, for example, applying the data filter DF to the updated patient data PD for generating at least one updated item of individual information EI (optional step S131-1). The updated item of individual information EI can then be compared with the item of individual information EI (optional step S131-2), whereupon in a further optional step S131-3, a clinical relevance is determined on the basis of the comparison of the updated individual information EI with the individual information EI, with the clinical relevance being all the greater, the more the updated individual information EI deviates from the individual information EI.

In step S140, the updated medical report MB is then distributed in the medical network 10. In particular, the medical report MB can be communicated to the front-end computing facility 50.

In step S140, at least one further application instance different from the front-end computing facility 50 can optionally be ascertained in the medical network 10, in which the medical report MB was used (optional sub-step S141). In this connection "was used" can mean, for example, seen by a user, saved, loaded into a viewer application and the like. An application instance can accordingly designate a user, a front-end computing facility 50 and/or storage facility 60, etc. In a further optional sub-step S142, the updated medical report MB is communicated to the at least one application instance.

The medical report MB can be distributed or communicated on the basis of the optional assessment of relevance in step S131. It can be provided in particular that the updated medical report MB is only communicated to the front-end computing facility 50 and/or further application instances within the medical network 10 when, in accordance with the evaluation of the clinical relevance in step S131, there is a change between the medical report MB and the updated medical report MB, which is clinically relevant (when there is, for example, a deviation in one or more item(s) of individual information EI above a specified threshold value).

Figure 9:
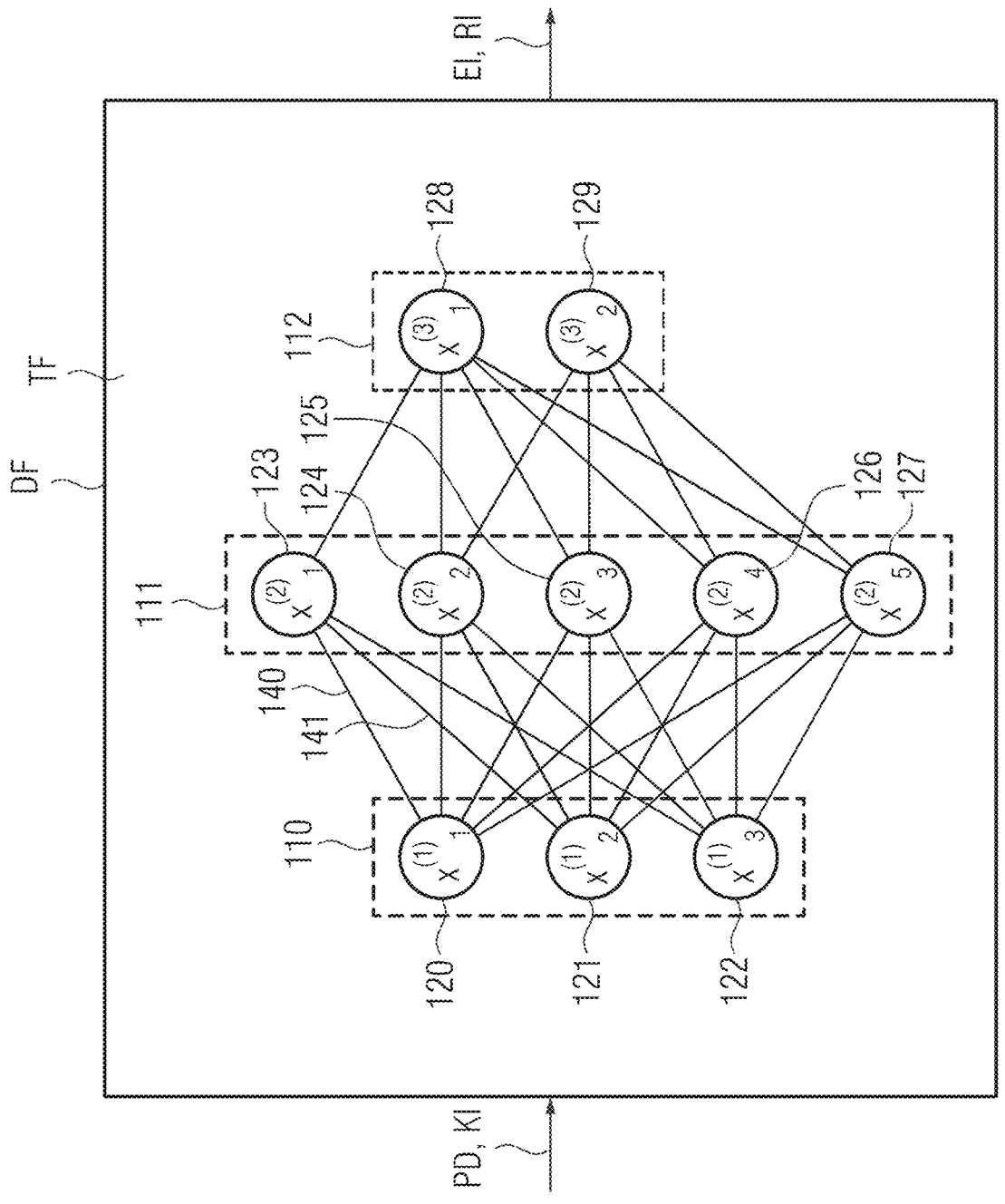
FIG. 9 shows a schematic representation of a use of a trained function in a data filter for providing a medical diagnosis from patient data according to one embodiment.

FIG. 9 represents a further embodiment of the data filter DF. In this embodiment, the data filter DF and/or individual filter components FK-1, FK-2, FK-3, . . . , FK-N are configured at least partially as a trained function TF. In the exemplary embodiment shown, the trained function TF is formed as a neural network. The neural network can also be referred to as an artificial neural net, artificial neural network or neural network.

The neural net 100 comprises nodes 120, . . . , 129 and edges 140,141, with each edge 140,141 being a directed connection of a first nodes 120^ . . . , 129 to a second nodes 120, . . . , 129. In general, the first node 120, . . . , 129 and the second node 120, . . . , 129 are different nodes. It is also possible that the first node 120, . . . , 129 and the second node 120, . . . , 129 are identical. An edge 140,141 from a first node 120, . . . , 129 to a second node 120, . . . , 129 can also be referred to as an incoming edge for the second node and as an outgoing edge for the first node 120, . . . , 129.

The neural net 100 responds to input values x(1)1, x(1)2, x(1)3 relating to a large number of input nodes 120, 121, 122 of the input layer 110. The input values x(1)1, x(1)2, x(1)3 are applied to generate one or a large number of output(s) x(3)1, x(3)2. The node 120 is connected to the node 123, for example via an edge 140. The node 121 is connected to the node 123, for example via the edge 141.

The neural net 100 learns in this exemplary embodiment in that it adjusts the weighting factors wi,j (weights) of the individual nodes on the basis of training data. Possible input values x(1)1, x(1)2, x(1)3 of the input nodes 120,121,122 can be, for example, the patient data PD and/or the context information KI.

The neural net 100 weights the input values of the input layer 110 on the basis of the learning process. The output values of the output layer 112 of the neural net 100 preferably correspond to an item of individual information EI, on the basis of which the medical report MB may be provided. The output can take place via an individual or a large number of output node(s) x(3)1, x(3)2 in the output layer 112.

The artificial neural net 100 preferably comprises a hidden layer 111, which comprises a large number of nodes x(2)1, x(2)2, x(2)3. A plurality of hidden layers can be provided, with a hidden layer using output values of another hidden layer as input values. The nodes of a hidden layer 111 perform mathematical operations. An output value of a node x(2)1, x(2)2, x(2)3 corresponds to a non-linear function f of its input values x(1)1, x(1)2, x(1)3 and the weighting factors wi,j. After receiving input values x(1)1, x(1)2, x(1)3, a node x(2)1, x(2)2, x(2)3 carries out a summation of a multiplication of each input value x(1)1, x(1)2, x(1)3, weighted with the weighting factors wi,j, as determined by the following function:

$$x_j^{(n+1)} = f\left(\Sigma_i x_i^{(n)} \cdot w_{i,j}^{(m,n)}\right).$$

The weighting factor wi,j can in particular a real number, in particular can lie in the interval of $[-1;1]$ or $[0;1]$. The weighting factor $$w_{i,j}^{(m,n)}$$

designates the weight of the edge between the ith node of an mth layer 110,11,112 and a jth node of the nth layer 110,111,112.

In particular, an output value of a node x(2)1, x(2)2, x(2)3 is formed as a function f of a node activation, for example a sigmoidal function or a linear ramp function. The output values $x(2)1$, $x(2)2$, $x(2)3$ are transferred to the output node(s) 128, 129. A summation of a weighted multiplication of each output value $x(2)1$, $x(2)2$, $x(2)3$ is calculated again as a function of the node activation f and therewith the output values $x(3)1$, $x(3)2$.

The neural network TF shown here is a feedforward neural network in which all nodes 111 process the output values of a previous layer in the form of their weighted sum as an input values. Of course other neural network types can also be inventively used, for example, feedback networks in which an input value of a node can simultaneously also be its output value.

The neural network TF can be trained by means of a method of supervised learning in order to provide the field information FI. A known procedure is back propagation, which can be applied to all exemplary embodiments of the invention. During training the neural network TF is applied to training input data or values and has to generate corresponding, previously known training output data or values. Mean square errors ("MSE") are iteratively calculated between calculated and expected output values and individual weighting factors are adjusted until the deviation between calculated and expected output values lies below a predetermined threshold.

It is possible to revert to empirical data in order to provide training data. It is thus conceivable, for example, to provide verified medical report MB and associated patient data PD or items of context information KI. A medical report MB can be verified, for example by a human user. The medical report MB can be created automatically, semi-automatically or entirely manually by one or more user(s).

Different data filters DF with different trained functions respectively can optionally also be provided for different case groups, which filters can be more high-performing in individual situations due to their greater degree of specialization than a data filter DF having a global trained function TF and mapping all of these conditions. In this case, as explained above, a selection step can be provided, which selects a suitable data filter DF for the respective application case.

The described embodiment of the trained functions TF used in the data filter DF should be understood as being merely exemplary. The trained function TF can of course have further intelligent algorithms and/or classification processes, such as a vector support machine, or an expert system, such as a Bayesian network. A Bayesian network can be designed, for example, to ascertain the individual information about the patient as a function of a probability model.

Figure 10:
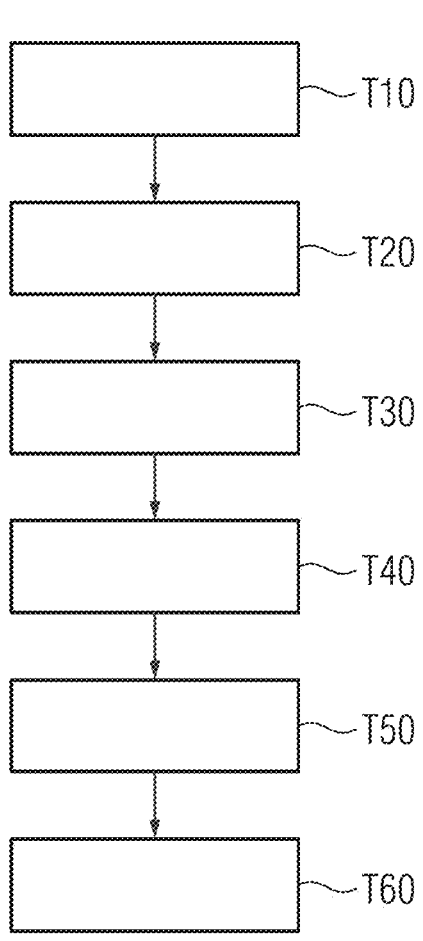
FIG. 10 shows a flowchart of a method for providing a trained function according to one embodiment.

FIG. 10 shows an exemplary embodiment of a computer-implemented method for providing a trained function TF. The order of the method steps is limited neither by the represented sequence nor by the chosen numbering. The order of the steps can thus possibly be interchanged and individual steps can be omitted. In addition, one or more step(s), in particular a sequence of steps, and optionally the entire method, can be carried out repeatedly.

Training input data is provided in step T10, with the training input data comprising training patient data PD and an item of associated training context information KI.

In step T20, training output data is provided, with the training output data being connected to the training input data, and in particular comprising a medical report MB, which was created in parallel with the provision of the training input data. Such a medical report MB is respectively based on a set having training patient data PD of a patient and associated training context information KI.

In a step T30, the trained function TF is applied to the training input data to generate intermediate output data. The intermediate output data corresponds to at least one item of individual information, on the basis of which a medical report is then to be created. The trained function TF can be pre-trained already, that is to say, one or more parameter(s) of the trained function TF have already been adjusted by the described training method and/or another training method. Alternatively, it is possible that the one or more parameter(s) of the trained function TF have not yet been adjusted by means of training data, in particular the one or more parameter(s) can be pre-allocated by a constant value and/or by a random value. In particular, it is possible that not all parameters of the trained function TF have been adjusted by means of training data yet, in particular all parameters can be pre-allocated by a constant value and/or by a random value.

In step T40, the intermediate output data is compared with the training output data, whereupon the trained function TF is adjusted in step T50 on the basis of the comparison. This can occur, for example, on the basis of a cost functional, which penalizes deviations in the field information FI in the intermediate output data from that in the training output data. One or more parameter(s) of the trained function TF can then be adjusted in particular such that the cost functional is minimized, for example, by means of a back propagation. In order to minimize the cost functional, different sets of pairs of training output data and training output data and intermediate output data are compared until a local minimum of the cost functional is reached and the trained function TF operates satisfactorily. Step T50 can in particular include extracting at least one item of individual information EI, corresponding to the intermediate output data, from the medical report MB provided as training output data and comparing it with the intermediate output data. In particular, on the basis of the intermediate output data, the medical report MB can be searched through according to this corresponding individual information EI, which is then compared with the intermediate output data. The trained function TF adjusted in this way is finally provided in step T60.

Figure 11:
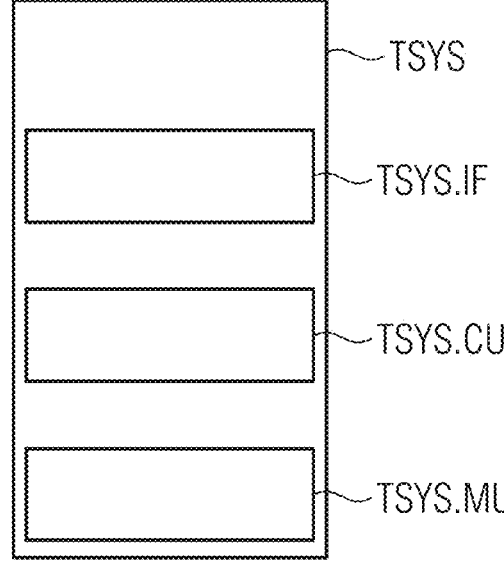
FIG. 11 shows a training system for training or providing a trained function.

FIG. 11 shows a training system ISYS for training a trained function TF. The represented training system ISYS is designed to carry out one or more of the inventive method(s). The training system ISYS comprises an interface TSYS.IF, a computing unit TSYS.CU and a memory unit TSYS.MU. The training system ISYS can in particular be a computer, a microcontroller or an integrated circuit. Alternatively, the training system ISYS can be a real or virtual group of computers (a technical term for a real group is "cluster", a technical term for a virtual group is "cloud"). An interface TSYS.IF can be a hardware or software interface (for example, PCI bus, USB or Firewire). A computing unit TSYS.CU can have hardware element or software elements, for example a microprocessor, an ASIC (acronym for "application-specific integrated circuit") or what is known as an FPGA (acronym for "Field Programmable Gate Array"). A microprocessor, FPGA and ASIC may be refered to as processing circuitry. A memory unit TSYS.MU can be implemented as a Random Access Memory (RAM for short) or as a permanent mass storage device (hard drive, USB stick, SD card, solid state disk). The training system TSYS represented here is designed to carry out the exemplary embodiments of the method for training a trained function TF in that the interface TSYS.IF and the computing unit TSYS.CU are designed to carry out the respective steps of the method.

In some example embodiments, the term 'module', 'interface' or the term 'unit' may be replaced with the term 'circuit.' As an example, the computation unit TSYS.CU may be part of, or include processor hardware (shared, dedicated, or group) that executes code and memory hardware (shared, dedicated, or group) that stores code executed by the processor hardware.

Figure 12:
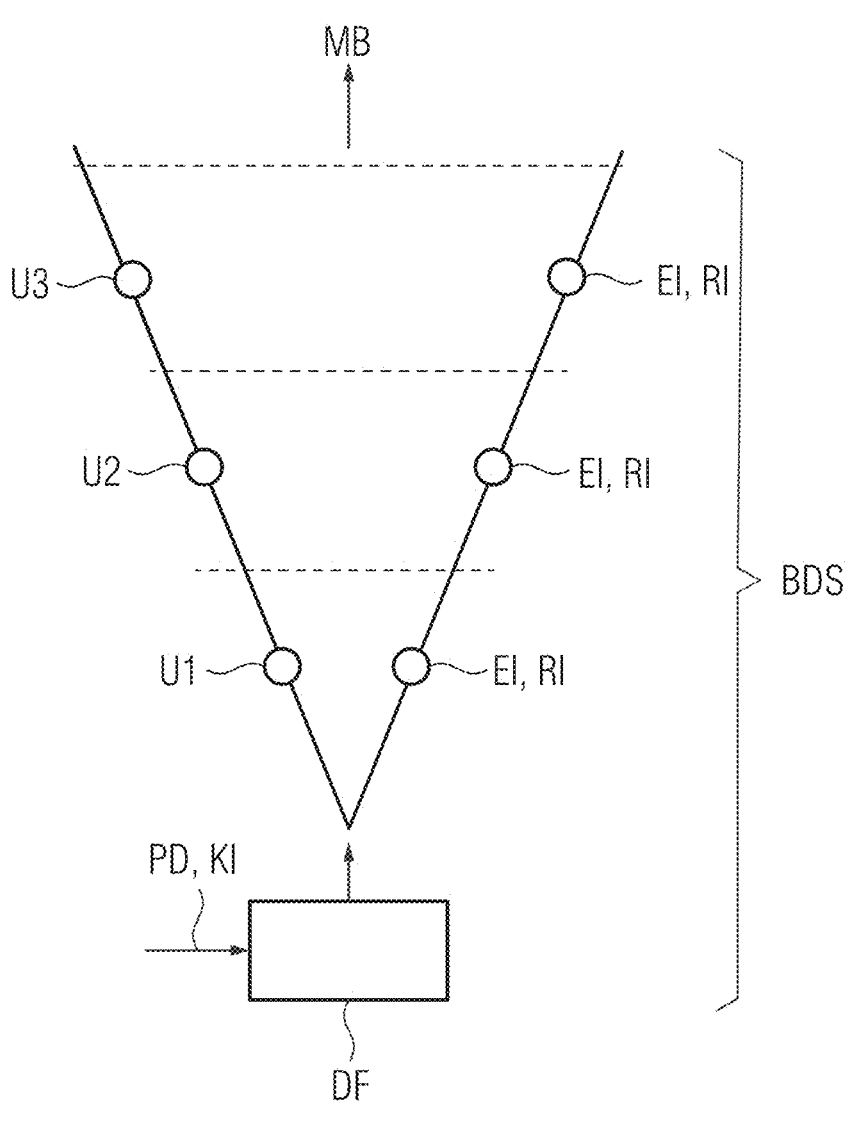
FIG. 12 shows a schematic representation of a report data structure for providing a medical report according to one embodiment.
Figure 12:
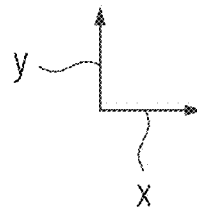
Figure 13:
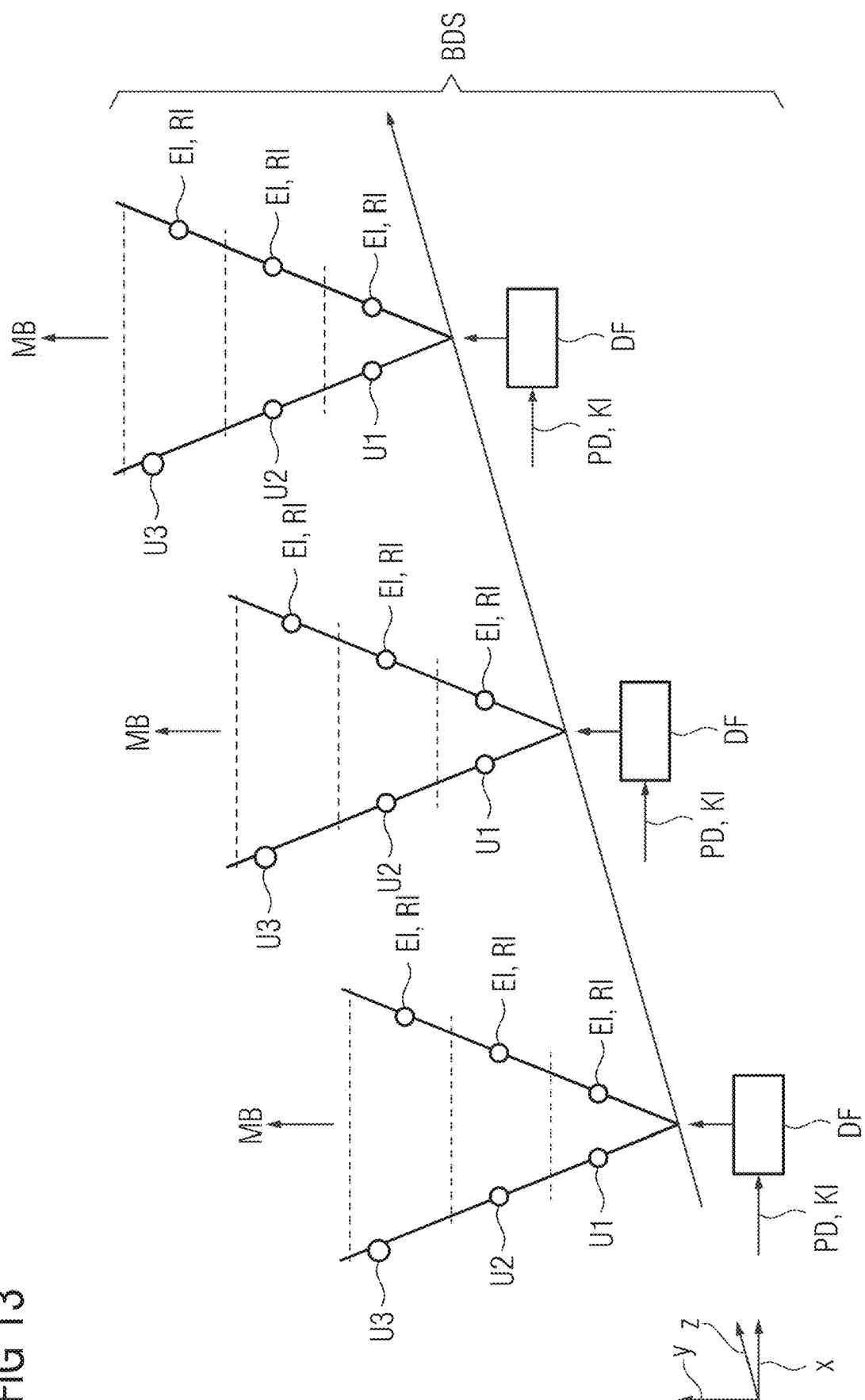
FIG. 13 shows a schematic representation of a report data structure for providing a medical report according to one embodiment.

FIGS. 12 and 13 schematically represent inventive processing for providing a medical report MB. The inventive linking of patient data PD, data filters DF and (if present) existing medical reports MB in the back-end computing facility 200 can be conceived as a virtual report for a patient, which can be adjusted at any time to the respective circumstances (which are characterized by the items of context information KI), and be updated and retrieved. This makes it possible to synchronize clinical activities in the medical network with the creation of medical reports MB.

The use of adaptive data filters DF firstly makes it possible to extract at least one item of individual information EI from the patient data PD corresponding to the context information KI. The data filter DF acts in such a way that for the respective application case corresponding to the context information KI, the relevant items of individual information EI are identified and provided. The data filters DF can also be designed such that they ascertain an item of relevance information RI for each item of individual information EI, which item of relevance information indicates the clinical relevance of the respective item of individual information EI in the medical context, that is to say, on the basis of the context information KI. The relevance information RI can be ascertained on the basis, for example, of a comparison of the individual information EI with earlier items of individual information, by way of a comparison of the individual information EI with a medical guideline, by way of a comparison of the individual information EI with a medical ontology (such as Radlex), etc.

As FIG. 12 represents, embodiments of the invention can enable information linking and traceability firstly along at least two data processing axes. To a certain degree the left axis maps the clinical status of the patient. This status can comprise, for example, the examinations U1, U2, U3 that have been performed. Using the data filter DF it is possible to check along the y-axis whether required steps were applied in principle in the clinical routine in accordance with the clinical status in the patient data PD and were possibly provided in the correct order (coherence). Such steps can be directed, for example, toward the generation of an item of individual information and comprise, for example, a laboratory investigation or an examination with an imaging modality. It is thereby possible to identify, for example, whether all critical examinations U1, U2, U3 for the patient were performed or are at least provided in accordance with the context information KI. With the aid of the data filter DF it is then possible to check along the x-axis whether the corresponding items of individual information EI are available or not (completeness). A report data structure BDS results from this, on the basis of which a medical report MB relating to the respective instant can be derived. The data filters DF, items of context information KI, individual information EI or associated relevance information RI used for creating the respective data structure can likewise be stored in the report data structure BDS. Furthermore, user information can be saved in the report data structure BDS, which indicates in which application instances of a medical network 10 the report data structure BDS or information provided from it (such as a medical report MB) were used or are provided for use.

As FIG. 13 represents, embodiments of the invention can also supply a link along a further data processing axis (z-axis). The z-axis can be conceived, for example, as a time axis (or as an axis of different medical contexts). Different medical reports MB can be linked to each other by data filters DF in order, for example, to compare different medical reports MB of a patient with each other, to transform them into one another and/or to build them on one another.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Some application cases will be described below in which methods and apparatuses according to the exemplary embodiments are used.

Application case: status check starting from the most recent medical report MB:

reading in the report data structure BDS for the patient (of the most recent event in the z-direction, cf. FIG. 13);

providing updated/current patient data PD relating to the patient;

extracting at least one updated item of individual information EI from the updated patient data PD on the basis of the report data structure BDS (that is to say, in particular based on the data filter(s) DF, the context information KI, the item(s) of individual information EI and/or the associated item(s) of relevance information RI which are saved in the report data structure BDS) with a data filter DF, it being possible for the data filter DF to be provided in particular on the basis of the report data structure BDS (in particular the data filter(s) DF saved in the report data structure BDS can be selected and applied);

correlating the at least one updated item of individual information EI with the report data structure BDS (in other words, the at least one updated item of individual information is classified in the report data structure BDS or mapped thereon);

determining an item of change information on the basis of the step of correlating, which item of change information indicates a progression of an item of individual information EI;

(optionally) determining, on the basis of the step of correlating, at least one new item of individual information EI, with the new item of individual information EI being an item of individual information without equivalent in the report data structure BDS;

(optionally) evaluating a clinical relevance of the new and/or updated item of individual information EI;

(optionally) outputting the new and/or updated item of individual information EI to a user (optional based on the clinical relevance), optionally, proposal of more extensive actions based on the new and/or updated individual information EI;

(optionally) applying a new report data structure BDS on the basis of the new and/or updated individual information.

Application case: generation of a medical report MB automatically reading in the report data structure BDS of the patient (of the most recent event in the z-direction, cf. FIG. 13);

automatically creating a medical report MB on the basis of the read-in report data structure BDS (for example, by applying one or more suitable data filter(s) DF);

(optionally) checking the patient status for coherence (y-direction) and completeness (x-direction) in particular on the basis of the context information KI;

(optionally) providing an item of relevance information RI by evaluating the clinical relevance of at least one item of individual information EI, in particular by applying a suitable data filter DF;

(optionally) communicating the medical report MB to a user;

(optionally) communicating the relevance information RI and/or an evaluation of coherence and completeness to the user;

(optionally) receiving user feedback in respect of the medical report MB, the relevance information RI and/or the evaluation of coherence and completeness;

(optionally) adjusting the report data structure BDS on the basis of the user feedback.

Application case: automatically updating a report data structure BDS and/or a medical report MB by taking into account medical guidelines reading in the report data structure BDS of the patient (of the most recent event in the z-direction, cf. FIG. 13);

receiving a result of an examination U1, U2, U3 for providing and/or updating at least one new item of individual information EI (for example, an imaging examination of the patient that has been performed again);

updating the patient data PD of a patient on the basis of the new individual information EI;

updating the most recent report data structure BDS based on the new individual information EI, in particular by correlating the new individual information EI with the most recent report data structure BDS (mapping the new individual information onto the V-shaped data fields) and/or by applying at least one data filter DF to the updated patient data PD, with the at least one data filter DF preferably being in saved the report data structure BDS and being read out from the report data structure BDS for application to the updated patient data PD Application case: automatically forwarding relevant information from the report data structure BDS reading in the report data structure BDS of the patient (of the most recent event in the z-direction, cf. FIG. 13) determining one or more application instance(s) in the medical network 10, in particular on the basis of the application information preferably saved in the report data structure BDS providing a medical report MB based on the report data structure BDS communicating the medical report MB to the one or more application instance(s)

Where it has not yet explicitly occurred, but is expedient and within the meaning of the invention, individual exemplary embodiments, individual partial aspects or features thereof can be combined with each other or interchanged without departing from the scope of the present invention. Advantages of the invention described with reference to one exemplary embodiment also apply without being explicitly mentioned, and where transferrable, to other exemplary embodiments.

The invention claimed is:

1. A method for providing a medical report in a medical network having a first front-end computing facility and a back-end computing facility, the method comprising:

receiving context information based on a patient, the receiving receives the context information from the first front-end computing facility at the back-end computing facility;

providing patient data of the patient on the back-end computing facility;

providing at least one data filter using the back-end computing facility based on the context information, the at least one data filter being configured to extract at least one item of individual information from the patient data for generating a medical report;

generating the medical report based on the patient data and the context information using the back-end computing facility by applying the at least one data filter to the patient data;

communicating the medical report to the first front-end computing facility using the back-end computing facility;

providing an earlier version of the medical report for the patient on the back-end computing facility;

determining at least one earlier application instance of the earlier version of the medical report in the medical network, the at least one earlier application instance being a second front-end computing facility different from the first front-end computing facility; and automatically communicating the medical report to the at least one earlier application instance using the back-end computing facility, wherein the first front-end computing facility and the second front-end computing facility each include a user interface configured to receive input from a user related to the medical report.

2. The method of claim 1, wherein the providing the at least one data filter comprises:

providing a plurality of selection data filters in the back-end computing facility, the selection data filters being configured to extract different items of individual information respectively for creating different medical reports, and selecting the at least one data filter from the selection data filters.

3. A non-transitory computer-readable storage medium including readable and executable program segments, when executed by a computing facility, cause the computing facility to perform the method of claim 2.

4. The method of claim 2, wherein
the at least one data filter comprises a trained function, the trained function being configured to extract at least one item of individual information for generating a medical report based on the context information.

5. The method of claim 4, further comprising:
providing a selection of a plurality of selection templates for creating different medical reports, respectively; and
selecting a template from the plurality of selection templates based on the context information, wherein
the generating generates the medical report based on the template.

6. The method of claim 5, further comprising:
ascertaining an item of change information based on a comparison between the patient data and the earlier version of the medical report, the change information indicating how at least one condition of the patient has changed since an instance of the earlier version of the medical report, wherein the generating generates the medical report further based on the change information.

7. The method of claim 2, further comprising:

receiving a modified medical report from the first front-end computing facility on the back-end computing facility, the modified medical report being based on the medical report and the modified medical report includes one or more modifications compared to the medical report; and adjusting the at least one data filter based on a comparison between the modified medical report and the medical report.

8. The method of claim 1, wherein
the at least one data filter comprises a trained function, the trained function being configured to extract at least one item of individual information for generating a medical report based on the context information.

9. The method of claim 1, further comprising:
providing a selection of a plurality of selection templates for creating different medical reports, respectively; and
selecting a template from the plurality of selection templates based on the context information, wherein
the generating generates the medical report based on the template.

10. The method of claim 1, further comprising:
ascertaining an item of change information based on a comparison between the patient data and the earlier version of the medical report, the change information indicating how at least one condition of the patient has changed since an instance of the earlier version of the medical report,
wherein the generating generates the medical report further based on the change information.

11. The method of claim 1, further comprising:
ascertaining at least one missing item of individual information in the patient data based on at least one of the context information or the at least one data filter; and at least one of, (i) communicating a note relating to the at least one missing item of individual information to the first front-end computing facility, (ii) applying a data evaluation program for ascertaining the at least one missing item of individual information on the back-end computing facility, or (iii) prompting at least one of the first front-end computing facility or a different application instance in the medical network to ascertain the at least one missing item of individual information using the back-end computing facility.

12. The method of claim 11, wherein
the patient data comprises at least one medical image dataset,
the at least one missing item of individual information refers to a measured value to be extracted from the at least one medical image dataset, and
the data evaluation program is an image processing algorithm for extracting the measured value from the at least one medical image dataset.

13. The method of claim 11, wherein
the at least one missing item of individual information refers to an examination of the patient that has not been performed, and the prompting is performed, the prompting including prompting performance of a medical examination that has not been performed.

14. The method of claim 1, further comprising:
receiving a modified medical report from the first front-end computing facility on the back-end computing facility, the modified medical report being based on the medical report and the modified medical report includes one or more modifications compared to the medical report; and
adjusting the at least one data filter based on a comparison between the modified medical report and the medical report.

15. The method of claim 1, further comprising:
detecting an update event with respect to the medical report on the back-end computing facility;
updating the medical report in accordance with the update event to create an updated medical report; and
communicating the updated medical report to the first front-end computing facility,
wherein the update event comprises at least one of the following events,
providing updated patient data,
providing an adjusted data filter,
receiving an update request in the back-end computing facility from the medical network, or
expiration of a specified period since generation of the medical report.

16. A non-transitory computer-readable storage medium including readable and executable program segments, when executed by a computing facility, cause the computing facility to perform the method of claim 1.

17. The method of claim 1, wherein the back-end computing facility includes a memory configured to store the medical report and the automatically communicating the medical report to the at least one earlier application instance using the back-end computing facility includes forwarding the medical report from the memory of the back-end computing facility to the second front-end computing facility.

18. An apparatus for providing a medical report in a medical network having at least one front-end computing facility, wherein the apparatus is connected to a first front-end computing facility via the medical network, the apparatus comprising:
a back-end computing facility, the back-end computing facility configured to cause the apparatus to,
receive context information based on a patient, the context information being from the first front-end computing facility,
provide patient data of the patient,
provide at least one data filter based on the context information, the at least one data filter being configured to extract at least one item of individual information from the patient data for generating a medical report,
generate the medical report based on the patient data and the context information by applying the at least one data filter to the patient data,
communicate the medical report to the first front-end computing facility,
provide an earlier version of the medical report for the patient on the back-end computing facility,
determine at least one earlier application instance of the earlier version of the medical report in the medical network, the at least one earlier application instance being a second front-end computing facility different from the first front-end computing facility, and
automatically communicate the medical report to the at least one earlier application instance using the back-end computing facility,
wherein the first front-end computing facility and the second front-end computing facility each include a user interface configured to receive input from a user related to the medical report.

* * * * *